(12) United States Patent
Vergara et al.

(10) Patent No.: US 10,648,770 B2
(45) Date of Patent: May 12, 2020

(54) MANUAL ACTUATORS FOR THERMOELECTRIC MODULES AND RELATED METHODS

(71) Applicant: Grace Engineering Corp., Memphis, MI (US)

(72) Inventors: David L. Vergara, White Lake, MI (US); Cody Schulz, Harrison Township, MI (US)

(73) Assignee: Grace Engineering Corp., Memphis, MI (US)

( * ) Notice: Subject to any disclaimer, the term of this patent is extended or adjusted under 35 U.S.C. 154(b) by 0 days.

(21) Appl. No.: 16/202,930

(22) Filed: Nov. 28, 2018

(65) Prior Publication Data
US 2019/0078857 A1    Mar. 14, 2019

Related U.S. Application Data

(63) Continuation-in-part of application No. 15/893,037, filed on Feb. 9, 2018, now Pat. No. 10,302,393, which is a continuation-in-part of application No. 15/374,112, filed on Dec. 9, 2016, now Pat. No. 10,094,638, which is a continuation of application No. 14/644,718, filed on Mar. 11, 2015, now Pat. No. 9,528,796.

(60) Provisional application No. 62/594,097, filed on Dec. 4, 2017, provisional application No. 62/460,131, filed on Feb. 17, 2017, provisional application No.
(Continued)

(51) Int. Cl.
| | | |
|---|---|---|
| F41G 1/38 | (2006.01) | |
| F41G 1/34 | (2006.01) | |
| H01L 35/32 | (2006.01) | |
| H01L 35/30 | (2006.01) | |
| H01L 35/18 | (2006.01) | |
| F41C 23/16 | (2006.01) | |
| F41B 5/14 | (2006.01) | |
| F41G 1/467 | (2006.01) | |
| A61B 5/0408 | (2006.01) | |

(52) U.S. Cl.
CPC ............ *F41G 1/345* (2013.01); *F41B 5/1403* (2013.01); *F41C 23/16* (2013.01); *H01L 35/18* (2013.01); *H01L 35/30* (2013.01); *H01L 35/32* (2013.01); *A61B 5/0408* (2013.01); *F41G 1/38* (2013.01); *F41G 1/467* (2013.01)

(58) Field of Classification Search
CPC ......... A61B 5/0408; H01L 35/30; F21L 13/00
USPC .................................................. 89/1.42, 1.12
See application file for complete search history.

(56) References Cited

U.S. PATENT DOCUMENTS

| | | |
|---|---|---|
| 4,470,263 A | 9/1984 | Lehovec et al. |
| 5,097,828 A | 3/1992 | Deutsch |
| 5,149,575 A | 9/1992 | Soifer |

(Continued)

FOREIGN PATENT DOCUMENTS

| | | | | |
|---|---|---|---|---|
| CA | 2954586 A1 | * | 1/2015 | ......... H05B 33/0803 |
| FR | 3029616 A1 | | 12/2014 | |

*Primary Examiner* — Stephen Johnson
(74) *Attorney, Agent, or Firm* — Warner Norcross + Judd, LLP

(57) ABSTRACT

A grasping element is provided including a manual actuator associated with a thermoelectric module, and an optional device powered by the thermoelectric module upon manipulation of the manual actuator. The thermoelectric module can generate electricity via a thermal gradient generated by a user's body. The electricity can power the optional device directly and/or indirectly.

20 Claims, 24 Drawing Sheets

Related U.S. Application Data

62/025,092, filed on Jul. 16, 2014, provisional application No. 61/968,069, filed on Mar. 20, 2014.

(56) References Cited

U.S. PATENT DOCUMENTS

| | | |
|---|---|---|
| 5,483,362 A | 1/1996 | Tai et al. |
| 5,519,591 A | 5/1996 | McCrary |
| 6,461,752 B1 | 10/2002 | Leung |
| 6,807,742 B2 | 10/2004 | Schick et al. |
| 7,509,998 B1 | 3/2009 | Rodney |
| 7,921,570 B1 | 4/2011 | Pulkrabek et al. |
| 8,231,240 B1 | 7/2012 | Rubio et al. |
| 8,443,541 B2 | 5/2013 | Elpedes et al. |
| 8,464,700 B2 | 6/2013 | Smith et al. |
| 8,619,238 B2 | 12/2013 | Overstreet |
| 9,146,077 B2 | 9/2015 | Moore et al. |
| 9,170,079 B2 | 10/2015 | Moore |
| 9,176,529 B2 | 11/2015 | Hata |
| 9,182,194 B2 | 11/2015 | Moore |
| 9,188,407 B2 | 11/2015 | Moore et al. |
| 9,243,865 B1 | 1/2016 | Bruhns |
| 9,297,614 B2 | 3/2016 | Moore |
| 9,453,702 B2 | 9/2016 | Bruhns |
| 9,553,475 B2 | 1/2017 | Boysen, III et al. |
| 9,723,659 B2 * | 8/2017 | Makosinski ............ H01L 35/30 |
| 9,755,131 B2 | 9/2017 | Schneider et al. |
| 10,021,236 B2 | 7/2018 | Esenwein et al. |
| 2006/0162225 A1 | 7/2006 | Danielson |
| 2006/0254638 A1 | 11/2006 | Carmeli et al. |
| 2007/0197885 A1 | 8/2007 | Mah et al. |
| 2009/0283126 A1 * | 11/2009 | Rostek .................... F01N 5/025 136/203 |
| 2009/0293855 A1 * | 12/2009 | Danielson ................ F41G 1/35 124/87 |
| 2010/0274162 A1 | 10/2010 | Evans |
| 2011/0268153 A1 | 11/2011 | He et al. |
| 2011/0284047 A1 | 11/2011 | Johnson et al. |
| 2013/0137957 A1 * | 5/2013 | Wood .................. A61B 5/0402 600/391 |
| 2013/0161343 A1 | 6/2013 | Ferron et al. |
| 2014/0049950 A1 | 2/2014 | Vazquez |
| 2014/0163394 A1 | 6/2014 | Katz |
| 2016/0143802 A1 | 5/2016 | Tranfaglia et al. |
| 2016/0154484 A1 | 6/2016 | Kampf |

* cited by examiner

MANUAL ACTUATORS FOR THERMOELECTRIC MODULES AND RELATED METHODS

CROSS-REFERENCE TO RELATED APPLICATIONS

This application claims benefit of U.S. Provisional Application 62/594,097, filed Dec. 4, 2017; and is a continuation-in-part of U.S. patent application Ser. No. 15/893,037, filed Apr. 18, 2018, now U.S. Pat. No. 10,302,393, which claims benefit of U.S. Provisional Application 62/460,131, filed Feb. 17, 2017, and of which U.S. patent application Ser. No. 15/893,037 also is a continuation-in-part of U.S. patent application Ser. No. 15/374,112, filed Dec. 9, 2016, now U.S. Pat. No. 10,094,638, which is a continuation of U.S. patent application Ser. No. 14/644,718, filed Mar. 11, 2015, now U.S. Pat. No. 9,528,796, which claims benefit of U.S. Provisional Application 61/968,069, filed Mar. 20, 2014 and U.S. Provisional Application 62/025,092, filed Jul. 16, 2014, which are all hereby incorporated by reference.

BACKGROUND OF THE INVENTION

The present invention relates to manual actuators, and more particularly to manual actuators associated with a thermoelectric module.

The popularity and use of archery equipment and firearms, for hunting, target shooting, and other dynamic shooting sports, has increased over the past several decades. The competitive nature of shooting and the desire by hunters to have well placed, ethical shots, has led to the development and commercialization of a variety of devices that facilitate the accuracy of a shot. One such device can be an aiming device, such as those including fiber optics, light gathering sight pins, illuminated reticles for rifle scopes or red dot illuminated sights.

Often, aiming devices are illuminated by a light source powered directly by a battery. An issue with these types of battery powered light sources is that the battery eventually dies. This can be particularly problematic when a once in lifetime shot presents itself or during a shooting competition. In military applications, soldiers also need aiming devices on their weapons to perform at a particular instant, and to always perform well. If they do not—due to latent or delayed activation or battery failure—it could result in catastrophe.

SUMMARY OF THE INVENTION

A grasping element including a manual actuator associated with a thermoelectric module, and an optional device powered by the thermoelectric module upon manipulation of the manual actuator, is provided. The thermoelectric module can generate electricity via a thermal gradient. The electricity can power the optional device directly and/or indirectly.

In one embodiment, the grasping element can be configured so that the thermoelectric module and any associated circuitry is mounted to and/or in the grasping element, for example, a hand grip, stock, handle, fore end or other component. This grasping element can be joined with an optional projectile shooting device. The grasping element can enable a user to grasp, hold, steady, aim, retain and/or manipulate (collectively referred to herein as grasp) the projectile shooting device or another device having such a grasping element, such as a spotting scope, a camera, a rangefinder or similar items powered in part or whole by electricity.

In another embodiment, the manual actuator of the grasping element can be a manually moveable element that can be engaged by a portion of a user's appendage to selectively transfer energy from the user's appendage to the device and its components. The manually moveable element can be in the form of an actuator lever that is movably coupled to a portion of the grasping element, optionally distal from the thermoelectric module.

In yet another embodiment, the grasping element can include a housing having an exterior. The manual actuator can be movably disposed adjacent and/or on the exterior in a first location. The thermoelectric module can be disposed adjacent and/or on the exterior in a second location distal from the first location. The manual actuator can be selectively engageable by a first portion of a user's appendage, while the thermoelectric module can have thermal energy transferred to it by a second portion of the user's appendage.

In still another embodiment, the grasping element can include an interior compartment can house the thermoelectric module, as well as circuitry associated with the thermoelectric module and/or manual actuator, to optionally meter and/or control communication of generated electricity to the device.

In yet another embodiment, the thermoelectric module can be in the form of at least one of a thermoelectric generator (TEG), a Seebeck device, a thermoelectric cooler (TEC) and a Peltier module. The thermoelectric module can generate electricity based on a thermal gradient existing about the module. For example, a thermal gradient can exist between a warm hand or other appendage of a user, and a colder component of a grasping device, optionally associated with a projectile shooting device. Thermoelectric generation of electricity can occur with either variation of thermal gradient, that is, electricity generation can occur when one side or surface of the module is either hotter or colder than its surrounding environment, or other components near it.

In yet another embodiment, the thermoelectric module can be in electrical communication with a circuit comprising a voltage booster, optionally disposed in the interior compartment of the grasping element. The voltage booster can be configured to provide a voltage output in the range of about 2 to 12 Volts, or other ranges, depending on the device and associated power requirements.

In yet another embodiment, the grasping element can include the thermoelectric module at least partially exposed on and/or near an exterior of the grasping element. The grasping element can optionally include multiple thermoelectric modules disposed in one or more locations on or near the exterior. There also can be multiple grasping elements with multiple thermoelectric modules. The thermoelectric module can be configured and/or oriented relative to the grasping element to contact at least one of a user's finger, thumb, palm, and cheek to receive thermal energy from a user's body during use.

In a further embodiment, the device can be an aiming device including a light source powered by the thermoelectric module. The aiming device can be distal from the grasping element. The light source can illuminate a sight element of a projectile shooting device to enhance visibility of the sight element in a variety of ambient lighting conditions, optionally in low light conditions. With the aiming device, a user can selectively illuminate a sight element of a projectile shooting device, optionally with the user's own body heat, to assist aiming the projectile shooting device during a shooting activity.

In another embodiment, the device can be a range finder device including a range finding unit. The range finder can be distal from the grasping element. The range finding unit includes components for determining a distance to a target object, including at least a light source, a light receiving unit, a distance calculation unit, and display unit. The range finder device may include additional components configured to provide additional information to a user, non-limiting examples of which include a temperature sensing unit, a wind speed sensing unit, a compass unit, and a unit for calculating a height of the target object. The thermoelectric module generates electricity from a thermal gradient generated when a user supplies thermal energy in the form of body heat to the thermoelectric module, optionally associated with the grasping element. The electricity generated by the thermoelectric module powers the range finding unit and optionally other components directly and/or indirectly. With the range finder device, a user can determine a distance to a target object, optionally with the user's own body heat.

In still a further embodiment, device can include a light source, and optionally can be an aiming device. The module can be in electrical communication with the light source. In some cases, the light source can be placed close enough to a fiber optic element, a red dot generator, a reticle, and/or a hologram generator of the aiming device so that upon illumination of a respective sight element, that sight element assists in aiming the device, for example, in less than desirable ambient light conditions. The thermoelectric module in this configuration can generate electricity for the illumination by heat that is generated by an appendage or other body part of the user physically contacting the module or some other element in thermal communication with the module.

In yet another embodiment, the device can be a range finder coupled to or including a thermoelectric module configured to determine a distance to a target object. The range finder device can include a light source, a light receiving unit, a distance calculating unit, and a display unit in electrical communication with the thermoelectric module. The thermoelectric module is adapted to power the light source so that the light source emits illumination toward the target object and to power the light receiving unit to detect the light emitted by the light source and reflected by the target object. The thermoelectric module is adapted to power the distance calculating unit to determine a distance to a target object based on the light detected by the light receiving unit and to power the display unit to display the calculated distance. The thermoelectric module is configured for mounting relative to manual actuator, optionally on a grasping element in a location such that thermal energy from a user's body is transferred to the thermoelectric module. The thermoelectric module is configured to generate electricity sufficient to power the light source, light receiving unit, distance calculating unit, and display unit as a result of thermal energy transformed from the user's body so as to communicate a distance to a target object.

In still another embodiment, the device can be coupled to a power source. The power source can be in electrical communication with the thermoelectric module such that the thermoelectric module provides electricity to the power source. The power source can be adapted to store energy and transfer the energy to the device and its components. The power source optionally can be in the interior compartment and/or distal from the grasping element, closer to or incorporated into the device.

In another, further embodiment, the device can couple to a secondary power source, such as a primary battery, which can be associated with the device and/or the grasping element. The thermoelectric module can serve to power the device by itself in some cases, or can serve as a back-up source of electricity in case of primary battery failure. Optionally, the thermoelectric module can serve as a redundant electricity generator to power the device and its components.

In still another embodiment, the device can include a power source. The power source can be electrically coupled to the thermoelectric module and/or a component of the device such as a light source. The electricity from the thermoelectric module powers and/or charges the power source. Optionally, the power source can be a capacitor and/or a battery, such as a rechargeable battery. The power source can provide electricity to the device. In this manner, the thermoelectric module indirectly powers the light source with electricity it generates that is stored in the power source.

In even another embodiment, the thermoelectric module directly powers the light source with electricity that the thermoelectric module generates. The module can be electrically coupled to the light source, and when the module generates electricity, that electricity can be transferred to the light source.

In yet another embodiment, the optional projectile shooting device can be a firearm, such as a handgun, a rifle, a shotgun or a machine gun. Optionally, the firearm can be in the form of a cannon. The firearm can be single shot, automatic or a semiautomatic. The firearm also can be mounted on a vehicle, watercraft or other mode of transportation. Further optionally, the projectile shooting device can be an archery bow, such as a compound bow, a recurve, a crossbow, or other device from which arrows or bolts can be shot.

In still yet another embodiment, the device can include one or more fiber optic elements. The fiber optic elements can be illuminated by a light source, and portions of the fiber optic elements can be disposed within a field of view of a user to serve as a sight element. As an example, an end of a fiber optic element can be included on a sight pin, reticle or other element and can generally face the user during use of the aiming device.

In a further embodiment, the device can include one or more reticles. The reticle can be illuminated by the light source, and disposed within a field of view of a user to serve as the sight element.

In still a further embodiment, the device can include one or more red dots. The red dot can be formed via a red dot generator, illuminated by the light source, and disposed within a field of view of a user to serve as the sight element.

In still another embodiment, the device can be a holographic sight system that generates a hologram within a field of view of a user to serve as the sight element. The hologram can be in the form of a reticle or other object, which can be built into and/or recorded in an optional viewing window, and can serve as the sight element.

In yet a further embodiment, the device can include one or more front and/or rear sights. The sights, or portions thereof, can be illuminated by the light source, and disposed within a field of view of a user to serve as the sight element.

In even a further embodiment, the thermoelectric module, optional power source, and light source can be included in head lamps, flash lights and other personal lighting devices, such as those utilized in the pursuit of hunting, fishing, hiking, spelunking or other activities.

In still another, further embodiment, a method is provided including: mounting a grasping element associated with a thermoelectric module on a projectile shooting device to create a thermal gradient as a result of the transfer of thermal energy from the user's body; generating electricity with the thermoelectric module due to the thermal gradient; actuating an actuator with the user's body to transfer the thermal gradient created electricity to a device; powering the device with the electricity; so that the user can utilize the device within a field of view while the projectile shooting device is in a shooting position.

In yet another, further embodiment a method is provided including: transferring thermal energy from a user's body to a thermoelectric module; generating electricity with the thermoelectric module due to the thermal gradient; powering a device with the electricity; illuminating the sight element with the light source so that the sight element is readily viewable in the user's field of view; aligning the sight element with a target; and optionally shooting a projectile at the target.

The current embodiments of the grasping element including a manual actuator associated with a thermoelectric module, provide benefits previously unavailable. For example, where the manual actuator is a actuator lever, it provides mechanical advantage to actuate a switch to convey electricity generated by a thermoelectric module. Further, where the actuator lever is utilized, it can be placed on the grasping element, which can be a hand grip, at a location comfortable for the user. In addition, the manual actuator can be disposed relative to the grasping element so that the manual actuator can be used ambidextrously. With the grasping element and manual actuator, a user can operate the device remotely from the grasping element, which can sometimes be more helpful than the user operating the device at the device itself. An example of this is the minimal hand movement that is required at the grasping element to either turn the device on or off, or alternatively control other functions of the device which are operable through the remotely located, manual actuator. Minimal hand movement to remotely control the device can be helpful when hunting, during home defense or in warfare.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

BRIEF DESCRIPTION OF THE DRAWINGS

FIG. 34 is a circuit diagram with the manual actuator in an on mode and thermal energy being used to charge a power source with an associated device being on.

DETAILED DESCRIPTION OF THE CURRENT EMBODIMENTS

A device of a current embodiment is shown in FIGS. 1-5 and generally designated 10. The projectile shooting device 1 as illustrated in those figures is generally in the form of an archery bow, for example, a compound archery bow. It will be appreciated, however, that the aiming device of the current embodiments can be used with any type of archery bow, including but not limited to a compound bow, a recurve bow, a crossbow, or other device from which arrows or bolts can be shot. Optionally, the projectile shooting device can be in the form of a firearm, including but not limited to a handgun (for example, a pistol and/or a revolver); a rifle (for example, a long rifle, a carbine, an assault rifle, a bolt pump rifle or a battle rifle); a shotgun (of any gauge) and/or a machine gun (for example, a machine pistol, a light machine gun, a mini gun, a medium machine gun or a heavy machine gun). The firearm can include any type of action, for example, bolt action, lever action, pump action and/or break action. The firearm can be single shot, automatic and/or semiautomatic. Further optionally, the firearm can be in the form of a vehicle-mounted weapon, mounted directly to the vehicle, a watercraft or other mode of transportation of course. As used herein, firearm can also include cannons, howitzers, handheld rocket launchers and similar weaponry, as well as equipment such as paint ball markers and air rifles such as bb guns, air soft guns and/or pellet guns.

As used herein, the term grip area can refer to an area on the projectile shooting device at which thermal energy from a user's body for example, a user's appendage, such as a hand, arm or cheek, can be transferred directly to a portion of the projectile shooting device, and ultimately to the thermoelectric module 20. A grip area can include a hand grip, a stock, a pistol grip, a cheek piece, a receiver or again any location on a firearm or archery bow that might be engaged by a user's appendage or body. A grip area also can include dedicated tabs or projections or areas on an aiming device or a projectile shooting device that do not provide or assist in holding the device in a shooting position. As an example, a bow sight of a bow, or a rifle sight or scope can include a simple projection extending outwardly from a main body. A thermoelectric module can be mounted therein or immediately adjacent that projection. A user can grasp or otherwise warm and transfer thermal energy to that projection, thereby causing the thermoelectric module to generate electricity. A battery or capacitor can store the generated electricity for a predetermined amount of time. Thus, a user need not necessarily transfer thermal energy directly to the thermoelectric module to power the light source during a shooting activity. For example, the user can pre-charge or store power in the power source before the shooting activity. That electricity can be later used when a target is presented.

Figure 1:
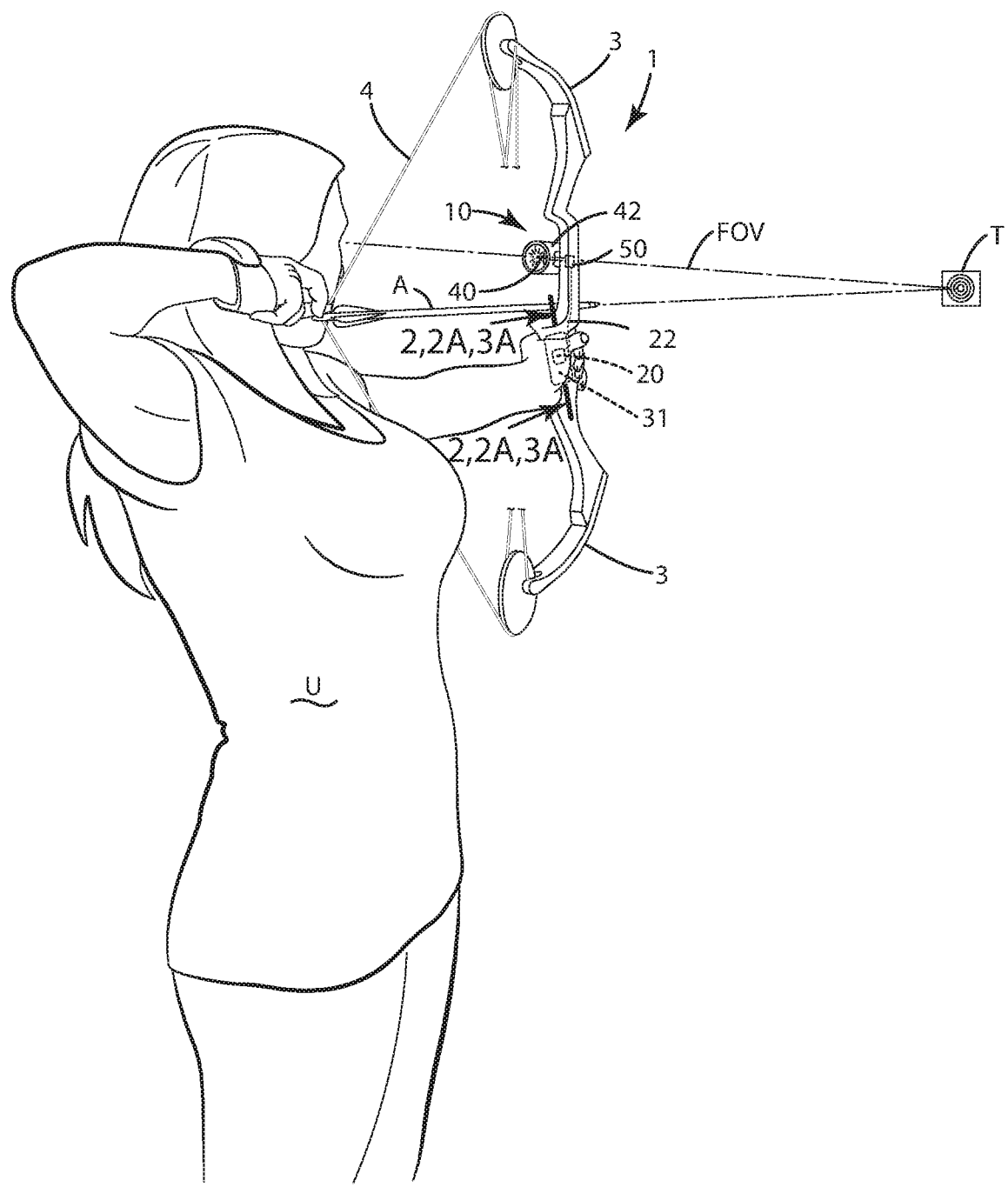
FIG. 1 is a perspective view of an aiming device of a current embodiment joined with a projectile shooting device, namely an archery bow.

Returning to the aiming device 10 mounted on an archery bow 1 shown in FIG. 1, the aiming device is generally mounted to a support structure 2. The support structure 2 as illustrated is a riser of the archery bow. In other embodiments, the support structure can be in the form of a stock of a crossbow, or a receiver, a barrel, a mount or other components of a firearm or other projectile shooting device. The aiming device and, in particular, the associated thermoelectric module, can be associated with, joined with or placed adjacent some type of thermally conducting member. As illustrated, this thermally conducting member can be in the form of a grip area, and in particular, a hand grip 31 of the archery bow 1. The hand grip typically is engaged by the user when holding or otherwise manipulating the archery bow.

As illustrated in FIG. 1, the thermoelectric module 20 can be mounted adjacent and/or within a grip area 31. Generally, the grip area 31 and optionally the thermoelectric module 20 can be mounted substantially below the aiming device 10 and more particularly the sight element 40 utilized by the user U when aiming at a target T. The distance by which the hand grip and/or thermoelectric module can be mounted below the aiming device 10, and optionally the sight element 40, can be at least about 1 inch, at least about 2 inches, at least about 3 inches, at least about 4 inches, at least about 5 inches, at least about 6 inches. Of course, other distances can be selected depending on the application. Moreover, with different constructions of an archery bow and/or firearm, the thermoelectric module 20 can be mounted above, beside or in other locations relative to the aiming device 10 and sight element 40.

Figure 2:
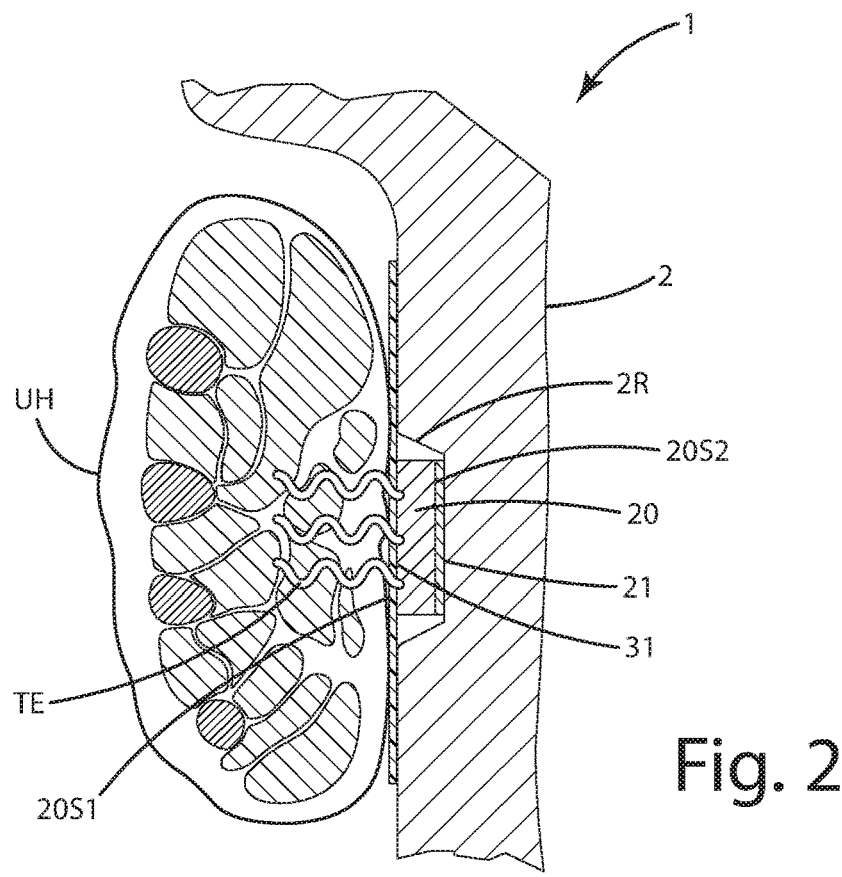
FIG. 2 is a section view of a thermoelectric module mounted to a support structure of the projectile shooting device taken along lines 2, 2A, 2B-2, 2A, 2B of FIG. 1.

The thermally conducting member shown as a grip area, in particular, a hand grip 31 in FIG. 2 can be configured to transfer thermal energy from a user's appendage to the thermoelectric module 20. In this manner, the thermoelectric module can be considered in thermal communication with the thermally conducting member. In the case of a crossbow or firearm, the thermally conducting member can be in the form of a stock, a fore end and/or a pistol grip that is engaged by the user when pointing or shooting the firearm.

Figure 2A:
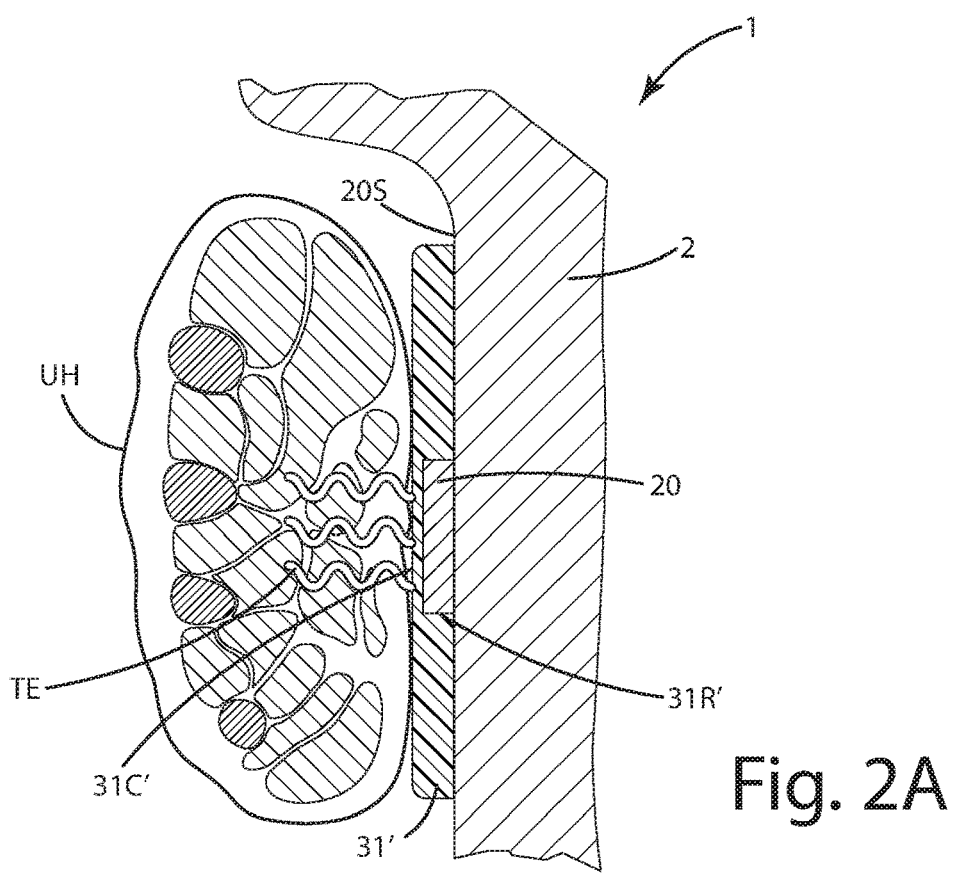
FIG. 2A is a section view of an alternative construction of a thermoelectric module mounted to the support structure taken along lines 2, 2A, 2B-2, 2A, 2B of FIG. 1.

As illustrated in FIGS. 2 and 2A, the thermally conducting member shown as the grip area 31 can be a thin sheet of metal, composite, polymer or other material which enables thermal energy TE from the user's appendage, for example, the user's hand UH, to penetrate therethrough and to transfer to the thermoelectric module 20. In some cases, the thermally conducting member 31 can be integrated directly into the thermoelectric module 20 in the form of a coating, cover or housing joined with the module 20.

Optionally, the thermally conducting member 31' can be in a construction shown in the alternative embodiment of FIG. 2A. There, the thermoelectric module 20 is disposed adjacent an outer surface 20S of the riser 2. The thermally conducting member 31' can be in the form of a grip area, in particular, a hand grip that is disposed at least partially around the riser 2. The grip can be of a particular thickness sufficient to define a recess 31R'. The thermoelectric module 20 can be disposed within the recess 31R'. When the grip area or thermally conducting member 31' is joined with the riser 2, the thermoelectric module 20, housed within the recess 31R' is placed immediately adjacent, and in some cases contacts, the riser 2 at the outer surface 20S of the riser 2. The thermoelectric module 20 is held in place within the grip area 31'. Opposite the outer surface 20S of the riser 2, the thermoelectric module 20 is covered by a thin cover 31C'. This thin cover 31C' and adjacent portions of the thermally conducting member surrounding the recess 31R' can facilitate or enable thermal communication between the user's hand UH so that thermal energy TE can be transferred from the user's hand or appendage to the thermoelectric module 20.

In either embodiment shown in FIGS. 2 and 2A, the thermoelectric module 20 can be disposed within the respective recesses 2R, 31R' using cement, adhesive, fasteners or other elements as desired. Of course, in some constructions, these elements can be eliminated all together with the thermoelectric module 20 being secured within the respective recess via a friction fit and/or simply by virtue of the larger thermally conducting member 31, 31' overlaying the thermoelectric module 20 and capturing it within a respective recess. Optionally, although shown as a recess defined in the riser of an archery bow 1, as will be appreciated, the recess 2R can be defined in any suitable stock or other component of a projectile shooting device, such as a recurve, cross bow or firearm component such as a stock, pistol grip, fore end, and other like components that can be readily grasped and gripped by a user to transfer thermal energy from the user's appendage to the thermoelectric module 20.

With reference to FIGS. 2 and 2A, it will be appreciated that in both embodiments, the user's body heat, for example that thermal energy TE generated by the user's hand UH, is primarily conveyed to a first surface 20S1 of the thermoelectric module 20. The user's appendage, for example, the user's hand UH transfers thermal energy TE to that first surface 20S1. The thermal energy is usually in the form of heat. As with most thermoelectric modules, for them to operate, they are placed adjacent a heat sink or a cooler surface to create a thermal gradient. That cooler surface 20S2 can be on or adjacent the opposite side of the thermoelectric module 20. This surface 20S2 can be cooled or otherwise used to create a thermal gradient by engaging the riser 2 or some other support structure of the projectile shooting device. Typically, the support structure can be constructed from a metal or a composite. Generally, the material from which it is constructed is of a colder temperature than the user's appendage in most ambient conditions. As an example, a user's appendage can be around 98° Fahrenheit. In hunting conditions, where the ambient temperature is about 0° Fahrenheit to 70° Fahrenheit, the support structure, for example, the riser 2 can be cooler than the user's appendage. Of course, in some cases, such as shooting competitions, or when firearms are heated up, the thermal gradient can be reversed. For example, the user's appendage at 98° Fahrenheit or so, can be less than the temperature of support structure, for example, the riser. As a more particular example, where a riser is colored black, and is used in a tournament in 90°, clear weather in full sun, the support structure or riser can heat up to 130°-150°. In this case, the thermal energy from the user, provided through the surface 20S1 to the module 20 can be less than the thermal energy or heat provided through the opposing surface 20S2 from the heat riser. Optionally, the thermoelectric module can be constructed so that even with this reversed thermal gradient, it can generate electricity. In most cases, however, the support structure can be cooler than the user's body, which results in the thermal gradient in which heat from the user's body is channeled toward the support structure, which in turn acts as a heat sink relative to the thermoelectric module 20 to generate electricity voltage and/or current flow. Again, the opposite of this operation is also contemplated herein.

Figures 6, 7:
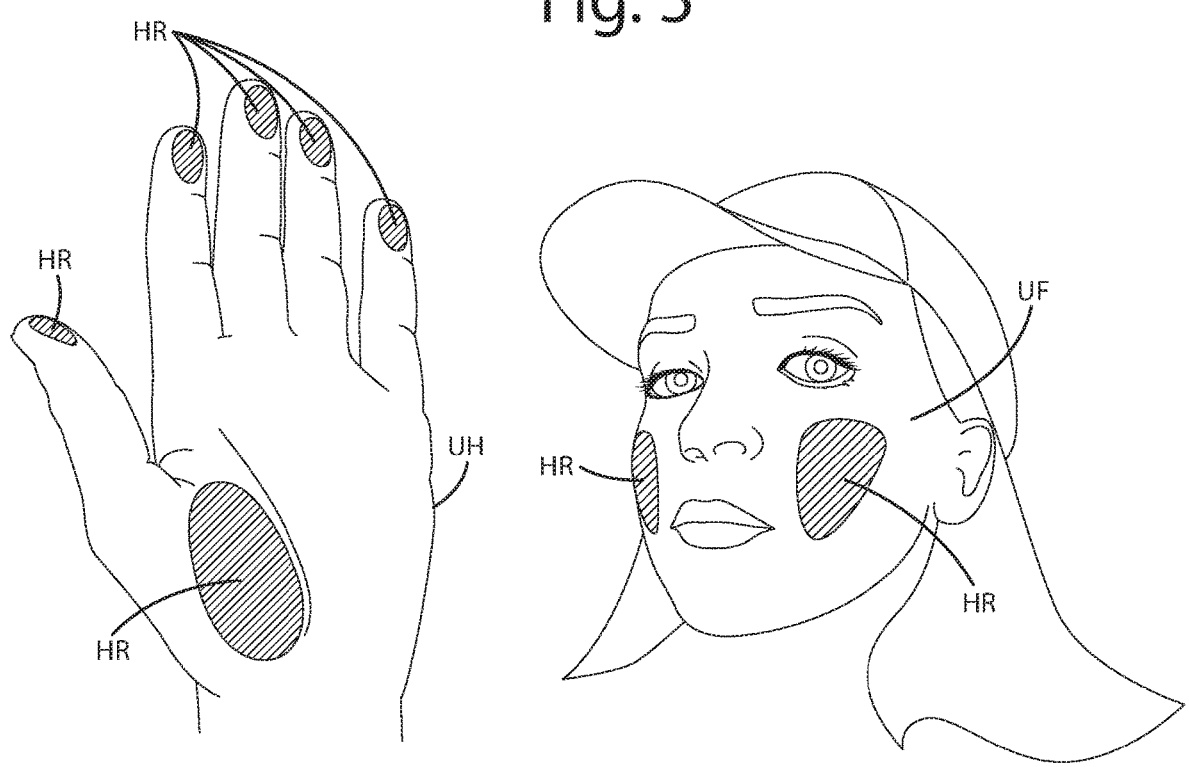
FIG. 6 is a view of a user's appendage, particularly a hand, showing areas of elevated heat generation.
FIG. 7 is a view of another user's appendage, namely a head, showing areas of elevated heat generation.

As mentioned above, a user's body generates the thermal energy that is transferred to the thermoelectric module so that the thermoelectric module can generate electricity to power the aiming device. As shown in FIG. 6, an appendage of the user U, specifically a user's hand UH, is illustrated. There, multiple heat generating regions HR are identified. These regions are generally the warmest or hottest parts of the hand. Accordingly, a particular grip or fore end of a projectile shooting device can be configured so that the thermoelectric module 20 is placed in close proximity to these heat regions HR. Examples of this placement are further illustrated in the description of the embodiments below, where the projectile shooting device is in the form of various firearms. It has also been discovered that the thermal energy generated from a user's face UF, as shown in FIG. 7, can be sufficient to create a thermal gradient to operate the thermoelectric module. As shown there, the user's face UF includes heat regions HR which are generally aligned with the cheeks of the user's face. Thus, a projectile shooting device, when in the form of a crossbow or firearm, can include a stock or other cheek piece in which the thermoelectric module is disposed. This can place a thermoelectric module in close proximity to the facial heat regions HR when a user is shooting and/or aiming the firearm, thereby efficiently transferring thermal energy to a thermoelectric module to ultimately illuminate an associated sight element of the aiming device.

Optionally, the support structure disposed adjacent the opposing surface 20S2 of the thermoelectric module can be constructed from plastic or a composite that is not a suitable heat conductor or heat sink. In such a case, a piece of metal acting as a heat sink can be located adjacent the second surface 20S2 of the thermoelectric module to act as a heat sink. This can be particularly used where the projectile shooting device support structure is constructed from wood or composite—such as a wood or synthetic stock of a firearm or a cross bow. Optionally, other heat sinks used instead of or in addition to metal can be graphite, carbon nanotubes, composites and/or special polymers.

Figure 2B:
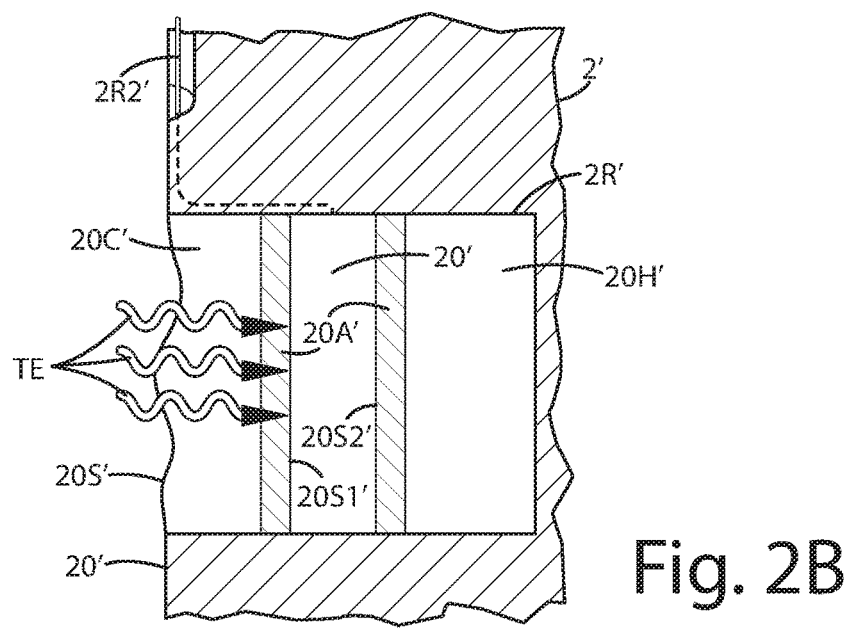
FIG. 2B is a section view of another alternative construction of a thermoelectric module mounted to the support structure taken along lines 2, 2A, 2B-2, 2A, 2B of FIG. 1.

An optional example of such a construction is illustrated in FIG. 2B. There, the thermoelectric module 20' can be embedded in or otherwise disposed in a recess 2R' of a support structure 2'. This support structure 2' can be the riser of a bow, or a stock of a cross bow, or a grip area such as a hand grip, stock, cheek piece or other component of a firearm or cross bow, or generally any other point of contact where a user may engage the support structure. In this construction, the support structure 2' can be a non-thermally conductive material such as wood or composite. In such a construction, the thermoelectric module 20' can be included in the recess 2R' with a secondary heat sink 20H'. The secondary heat sink 20H' can be disposed within the recess 2R' adjacent the second or inner surface 20S2' of the thermoelectric module 20'. If desired, the secondary heat sink 20H' can be adhered within the recess 2R'. Likewise, an adhesive 20A' can be disposed between the secondary heat sink and the thermoelectric module 20' to provide desired positioning and securement of the same. This adhesive 20A' can be thermally conductive so that it does not substantially impair the function of the thermoelectric module 20'.

Opposite the secondary heat sink 20H', adjacent the outer surface 20S1', a thermally conductive member 20C' can be disposed. This thermally conductive member 20C' can generally have less mass than the heat sink so that thermoelectric energy TE from a user's body can be efficiently transferred through the thermally conductive member 20C' to the thermoelectric module 20'. This thermally conducting member 20C' also can be adhered with an adhesive 20A' to the surface 20S1' and generally interfit within the recess 2R'.

The outer surface 20S' of the thermally conducting member 20C' can be contoured to approximate a feature of the user's body, for example, a palm, finger, cheek or the like, that provides the thermal energy TE ultimately to the thermoelectric module 20'. In other embodiments, the outer surface 20S' of the thermally conducting member 20C' can be contoured to approximate and generally match the outer surface 20' of the support structure 2'. For example, where the support structure 2' is a stock of a firearm, the outer surface 20' can generally smoothly and seamlessly transition to the outer surface 20S' of the thermally conducting member 20C' so that the thermally conducting member 20C' is not readily identifiable or provides a generally aesthetically pleasing appearance of the outer surface 20'. Optionally, the thermally conducting member 20C' can be deleted from the construction shown in FIG. 3. The outer surface 20S1' of the thermoelectric module 20' can be generally coextensive and/or contiguous with the outer surface 20' of the support structure 2'. Optionally, there can be a thin coating of a thermally conductive polymer or other material disposed on the outer surface 20S1' to protect it from the environment in certain applications.

FIG. 2B also illustrates a support structure 2' that defines a secondary recess 2R2' extending generally away from the thermoelectric module 20'. This secondary recess can generally conceal, house and/or protect an electric coupling element 22 extending away from the thermoelectric module 20' toward the light source and optionally other circuitry associated with the light source, as well as other optional electrical components of the aiming device. The secondary recess 2R2' can be in the form of a U- or V-shaped channel. The electrical coupling element 22 can be in the form of a wire, conductive cord, strip, band, tape or other electricity conducting structure. The secondary recess 2R2' can be defined by the outer surface 20' of the support structure 2'. It can extend over a length of the outer surface 20' to a location sufficient to establish electrical communication with the light source 50 and/or other circuit components of the aiming device 10. Generally, the thermoelectric module is mounted distal from the light source in most embodiments herein. For this reason, the thermoelectric module 20' is connected to the other elements of the aiming device with the electrical coupling element 20W'. Optionally, the secondary recess 2R2' can be covered with a cap or other type of closure or cover to conceal and/or protect the electrical coupling element 22 disposed therein.

The thermoelectric module 20 can be in the form of a thermoelectric generator (TEG), a Seebeck device, a thermoelectric cooler (TEC) and/or a Peltier module. Generally, the thermoelectric module generates electricity or voltage based on a thermal gradient existing about the module. For example, a thermal gradient can exist between a user's appendage, which generates thermal energy, and a cold metal, composite, polymeric or other heat sink of a projectile shooting device. Generation of electricity via the thermoelectric module can occur with either variation of the thermal gradient. Specifically, electricity generation can occur when one side or surface of the module is either hotter or colder than its surrounding environment or an opposing side or surface of the module as described above. One type of suitable thermoelectric power source is disclosed in U.S. Pat. No. 8,231,240 to Rubio entitled Surface Lighting Devices Having a Thermoelectric Power Source, which is hereby incorporated by reference in its entirety. This type of thermoelectric module, namely a TEG, includes a variety of different thermoelectric materials which can include metallic conductors such as, for example, bismuth and antimony. Other thermoelectric materials can include but are not limited to semiconductors, N-doped semiconductors, and P-doped semiconductors. Some suitable non-metallic thermoelectric materials can include, for example, bismuth chalcogenides, skuderite-type materials and complex oxide materials.

Figure 3:
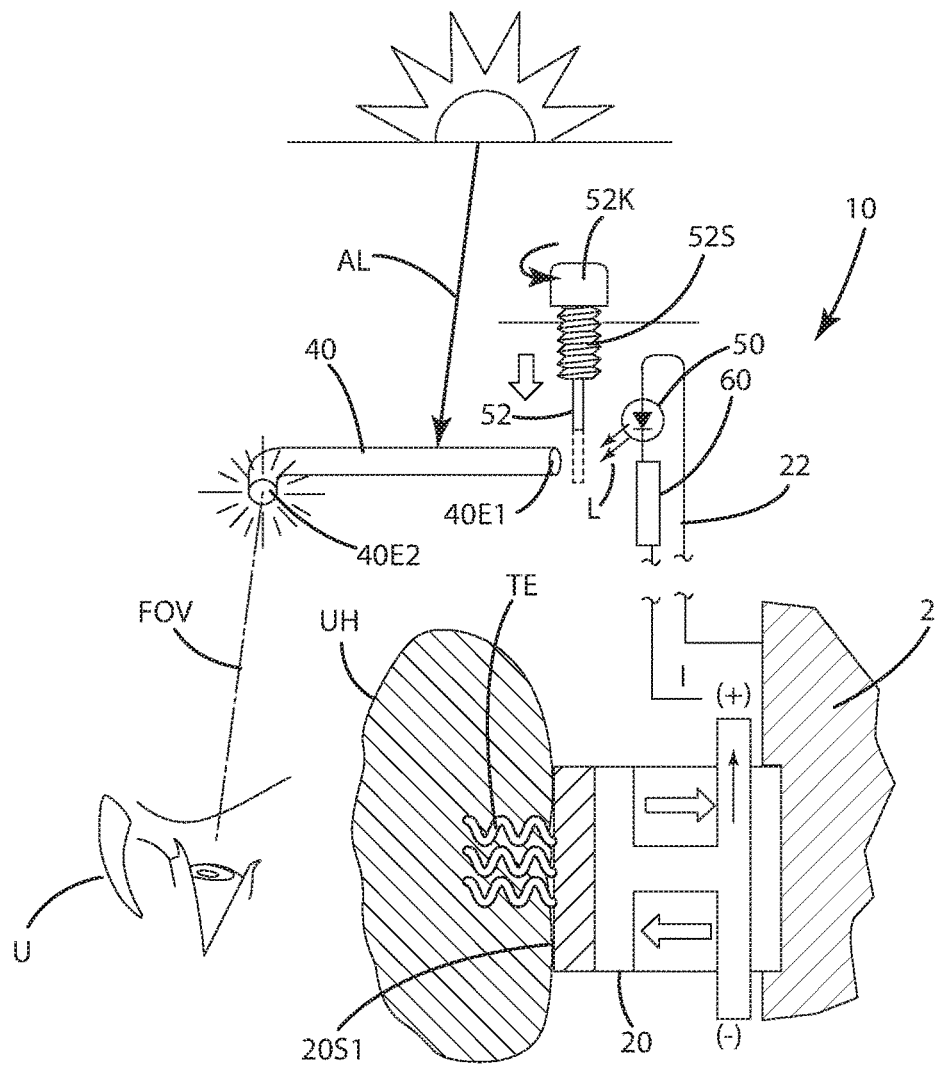
FIG. 3 is a schematic illustrating the various components of the aiming device of the current embodiment.

Generally the thermoelectric module 20 as shown in FIG. 3 operates as follows: a heat source, such as the user's hand UH, transmits thermal energy to the outer surface 20S1 of the thermoelectric module 20. A heat sink 2, for example, a metallic riser of a bow, causes a flow of heat or thermal energy TE from the user's hand toward the heat sink. As heat flows from the heat source, that is, the user's hand UH, toward the heat sink, that is, the riser 2, the charge carriers (e.g. electrons and/or holes) move in the direction of heat flow. Movement of the charge carriers results in an electric current I which moves through the electrical coupling element 22 which is described in further detail below. Ultimately, the electrical current I, also referred to as voltage and/or electricity herein, powers a light source 50. The light source 50 of the aiming device 10 can be a variety of different light sources.

As an example, light emitting diodes (LEDs), organic light emitting diodes (OLEDs), and/or laser diodes can be utilized as the light sources herein. Of course, the light sources can be provided in a variety of colors spanning the visible region of the electromagnetic spectrum. The light sources as utilized in the aiming devices can be continuously lit at a constant intensity when electricity is flowing thereto. Of course, depending on associated circuitry, the light source can be dimmed in response to varying light conditions rather than being turned off entirely. In some cases, the light sources can be configured to blink in a given pattern depending on the particular application.

As further shown in FIG. 1, the thermoelectric module 20 is in electrical communication with the light source 50 and/or other circuitry 60 of the aiming device 10 via an electrical coupling element 22. This electrical coupling element extends from the thermoelectric module toward the light source. As described further below, the electrical coupling element 22 can be on an outer surface of the support structure or mounted within a recess or channel defined by the outer surface of a support structure. Alternatively, the support structure might be hollow so that the electrical coupling element 22 extends through an internal cavity of the support structure.

As mentioned above, the light source 50 shown in FIGS. 1 and 3 can be in the form of an LED or other low voltage draw lighting element. If desired, the electrical requirements of the light source 50 can be selectively matched to the operation of the thermoelectric module 20. In some cases, as described further below, a voltage booster circuit can be utilized to assist in consistently providing electricity at a desired level to the light source 50, for example, when the light source is a laser diode. Generally, the light source 50 emits illumination L. The light source is placed in proximity to any one of a variety of sight elements 40. As explained in connection with the current embodiments, these sight elements can be fiber optic elements, red dot elements, reticles, holographic reticles/images or other indicia or sight items that a user U can align with a target T.

As further shown in FIGS. 1 and 3, at least in the context of an archery bow, the sight element 40 can be in the form of a fiber optic element. A fiber optic element can be constructed from a polymer and specially fabricated to reflect light conveyed through the sight element 40 from a first end 40E1 to a second end 40E2. The first end 40E1 can be disposed adjacent the light element 50 so that light L emitted by the light source 50 is projected at least partially if not substantially upon the end 40E1. The light then travels through the fiber optic element 40 to the end 40E2. As illustrated in FIG. 3, this end 40E2 appears illuminated. Thus, a user U can readily discern the illuminated end 40E2 within the user's field of view FOV. This can be helpful, particularly when ambient light conditions are of low light, for example, at dusk and dawn. With the illuminated end 40E2, the user's ability to appropriately align the sight element with game or a target can be enhanced.

Generally, this sight element, in the form of the fiberoptic element, and more particularly, its end 40E2, is disposed within the field of view FOV of the user U to serve as a sight element and align the projective shooting device with the target T. The end 40E2 can generally face the user during use of the aiming device, particularly when illuminated by a light source 50.

The sight element 40 in FIG. 3, in the form of a fiber optic element, can be disposed in or otherwise held or constrained by a sight pin, optionally constructed from metal composites or polymers, to protect the fiber optic element from the environment and to keep it satisfactorily aligned with a user's field of view. The sight pin can be mounted to a housing 42 as illustrated in FIG. 1. The housing itself can be part of an archery sight configured to be attached to the archery bow 1 with fasteners, brackets and/or other constructions.

Figure 4:
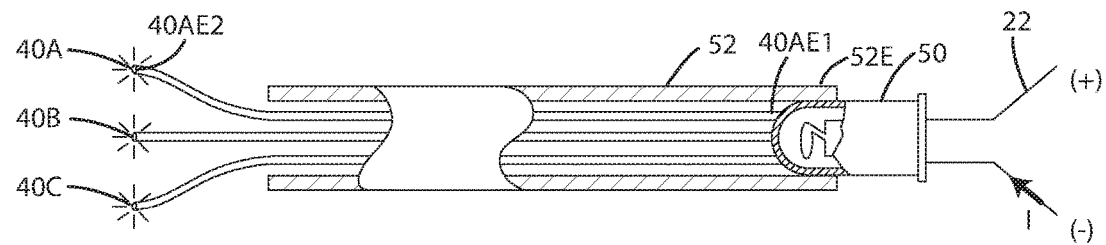
FIG. 4 is a partial section view of a light source and sight elements of the aiming device.

Depending on the application, a single sight element 40 can be illuminated by the light source 50 as shown in FIG. 3. If desired, however, multiple sight elements, optionally in the form of fiber optic elements, can be illuminated by the light source. This is illustrated in FIG. 4. There, the light source 50 is in the form of an LED. The LED is connected via an electrical coupling element 22 to circuitry and/or a thermoelectric module which provides electricity thereby causing the light source 50 to emit illumination. The light source 50 can be joined with a housing 52, which as illustrated, is in the form of a tube. This tube can optionally be constructed from a polymer, such as a heat shrinkable polymer or other polymer. The end 52E of the tube 52 can be disposed over at least a portion of the LED 50. Where the tube is heat shrinkable, this end 52E can be heated to secure the housing 52 to the light source 50. Within the housing or tube 52, multiple fiber optic elements 40A, 40B and 40C can be disposed. The first ends of these fiber optic elements, for example, 40A1 can be disposed immediately adjacent the outer rounded and/or spherical surface optional of the light source 50, particularly where the light source 50 is an LED. The fiber optic element 40A can extend through the housing or tube 52, and can be associated with a sight pin or other sight support so that the second end 40AE2 is readily visible to a user and within the user's field of view.

Figure 5:
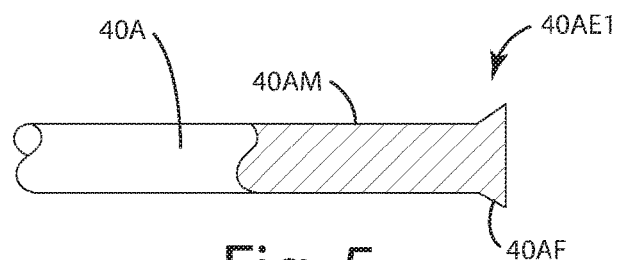
FIG. 5 is a close up partial section view of a sight element of the aiming device of the current embodiment.

Optionally, the ends of the fiber optic elements 40A, 40B, 40C can be specially bonded to the outer surface of the light source 50, for example, with an optically transmissive adhesive or other material. Further optionally, the ends of the fiber optic elements 40A-40C can be disposed adjacent the light source 50 and flared at the ends adjacent the light source 50. For example, as illustrated in FIG. 5, the end 40AE1 includes a flare 40AF. This flare can be joined with a main body portion 40AM of the fiber optic element 40A. The main body element 40AM can have a substantially uniform diameter and circumference. The main body 40AM can transition to the flare 40AF. At the flare, the diameter and the circumference around the exterior surface of the flare 40AF increases as it becomes more distal from the main body 40AM. Put another way, at the end 40AE1 of the fiber optic element 40A, the main body 40AM tapers from a smaller diameter or dimension to a larger diameter or dimension in the flare region 40AF, toward the large end of the element at the right of FIG. 5. The amount of flare and/or tapering can be selected depending on the light transmissive properties of the fiber optic element and/or the method of attachment to, or placement near, the light source 50. Generally, the flare can be configured to enhance light capture by the end of the fiber optic element so that more light is transferred to an opposite end of the element. The flare can also provide a physical structure so that the end near the flare can be physically constrained or captured by another element, such as an aperture, to precisely place the end.

The system and light source 50 herein can serve as a backup to illuminate a sight element when ambient light is insufficient, or when a light source is powered by a secondary power source, such as a battery, which can no longer power the light source due to failure of a battery. For example, as shown in FIG. 3, the fiber optic element 40, in the form of a sight element, can be illuminated by ambient light AL. This, in turn, illuminates the end 40E2 of the sight element 40 to enable a user to view it better within the user's U field of view FOV. When the ambient light decreases, for example, at dusk and dawn, it may be unable to sufficiently illuminate the end 40E2. In this case, the thermoelectric module light source and any associated circuitry can be powered on or actuated to supplement or replace the ambient light with the light L produced by the light source 50. Optionally, thermoelectric module can include an on/off switch described below to selectively turn on or off the light source 50 depending on the user's preferences, or a timer to automatically turn on/off the light source during expected times of low ambient light.

Further optionally, the light source 50 can be joined with a circuit 60 within which another power source is disposed. This power source can be in the form of a replaceable and/or rechargeable battery. When the replaceable/rechargeable battery, also referred to as a power source herein, fails, the circuitry can sense the failure and utilize electricity from the thermoelectric module 20 to alternatively power the light source 50. Thus, the thermoelectric module can operate as a backup source of electricity for the light source. Put another way, the thermoelectric module can serve as a redundant electricity generator to illuminate a sight element when there is insufficient power or electricity provided the light source.

As mentioned above, the light source 50 can output illumination L to illuminate the end 40E2 of the element 40. Optionally, the performance characteristics of the light source can be selectively regulated by a user using a selector that is manually operable by the user. For example, light intensity and/or other light characteristics generated by the light source 50 can be modulated in a variety of manners, for example, via a rheostat that regulates current by varying resistance, a potentiometer voltage divider and/or on/off switch, all of which are described further below.

In the embodiment shown in FIG. 3, the amount of light L reaching the sight element 40 also can be physically modulated using another type of selector. As illustrated, the aiming device 10 can include a shutter 52. The shutter 52 can be selectively moveable from the configuration in solid lines to the configuration shown in broken lines by a user. The shutter, when in the position shown in full lines, generally does not impair the amount of light L that reaches the end 40E1 of the sight element 40. Thus, a significant amount of the light L reaches the end 40E1 to illuminate the sight element 40. The shutter 52 can be coupled to a screw element 52S disposed in a housing (not shown). The screw element 52S can be joined with a knob 52K. The knob 52K can be manually adjustable by a user to effectively move the shutter 52 from the position shown in full lines to the position shown in broken lines. This can be affected by rotating the knob 52K in the direction of the arrow. This translates to linear movement of the shutter 52 downward, so that it is disposed between the light source 50 and the end 40E1. Thus, the amount of light L reaching the end 40E2 is diminished. In this manner, a user can selectively adjust the illumination output at the end 40E2 which again can be used to directly align the sight element with a target. In this construction, the light from the light source 50 can be modulated by simply shading the sight element in varying degrees relative to light emitted from the light source 50.

Figure 8:
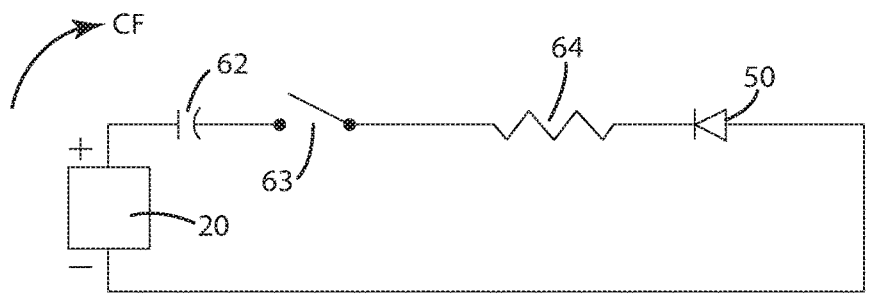
FIG. 8 is a diagram of a circuit for use with the aiming device.

The aiming device can include a circuit 60. This circuit can take on a variety of forms depending on the particular application and desired functionality of the aiming device. One example of a simple circuit that can be used with the aiming device is illustrated in FIG. 8. There, the circuit 60 includes the thermoelectric module 20, which for example, can be a Peltier module that generates current. The current flows in direction of the arrow CF to a capacitor 62. The electricity generated by the thermoelectric module 20 is stored in the capacitor 62. The circuit 60 also can include a switch 63. Closing the switch 63 allows the current to flow, in the direction of the arrow CF. The circuit also can include a resistor 64 and a light source 50. When the switch is closed, electricity flows through the resistor 64 to the light source 50, which optionally can be an LED. This causes the LED 50 to illuminate.

Although shown as including a capacitor 62, one type of power source, the circuit 60 can include a rechargeable battery, such as nickel cadmium or lithium rechargeable battery, another type of power source. Whatever the case, the capacitor or rechargeable battery can serve as a power source to store the electricity and provide current flow or electricity to the light source 50, even when thermal energy TE is not being transmitted directed to the thermoelectric module 20. Where a battery, rechargeable battery and/or capacitor is provided in the circuit 60 to provide electricity or voltage to the light source 50, the thermoelectric module 20 is considered to indirectly power the light source because, technically, the generated electricity is flowing from the battery or capacitor, that is, a power source. Where no battery or capacitor or other power source is included, the thermoelectric module is considered to directly power the light source, with the electricity flowing from that module to the light source, or in general to a device requiring electricity to power some feature or function. In either case, the generated electricity that came directly or indirectly from the thermoelectric module can be eventually transferred to the light source or device in general.

Figure 9:
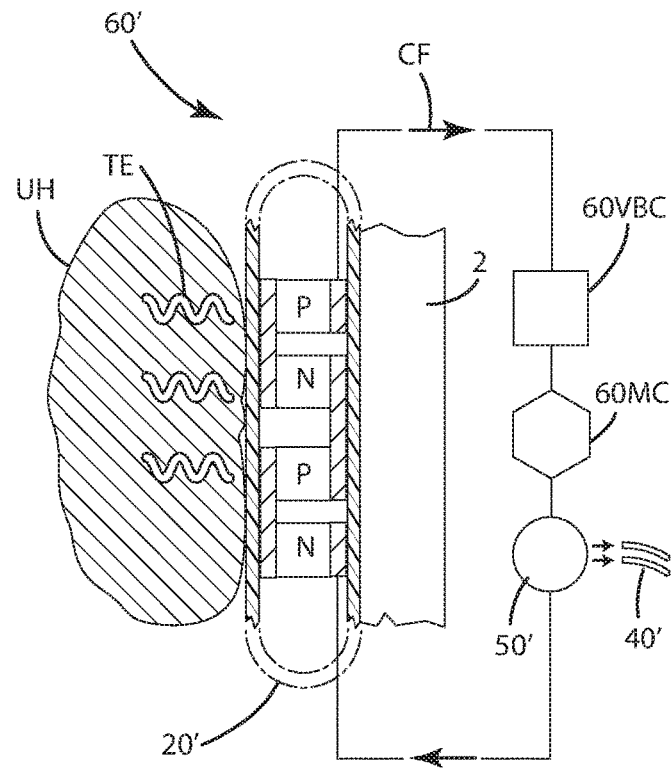
FIG. 9 is a diagram of an alternative circuit for use with the aiming device.

Another example of a circuit is illustrated in FIG. 9. There, the circuit 60' can be coupled to the thermoelectric module 20'. Current flows in the direction CF to a voltage booster circuit 60VBC. There, the voltage can be increased in a variety of manners to provide more voltage ultimately to the light source. Optionally, this can be useful where the light source is a laser diode or LCD. The booster circuit can include a DC/DC converter. It also can be unipolar, with voltages at fixed polarity only, or bipolar with voltage at either polarity. The circuit 60' also can include a light intensity modulation circuit 60MC. This light intensity modulation circuit can include a variety of different electrical components to modulate the current flow to the light source 50' and ultimately to the light L that is transmitted to the sight elements 40'. For example, the light intensity modulation circuit can include a rheostat that regulates the current flow by varying resistance. As another option, the light intensity modulation circuit can include a potentiometer voltage divider. As yet another example, this circuit 60MC can include a simple on/off switch. Other electrical components for modulating light intensity can be included in the modulation circuit 60MC.

Figure 10:
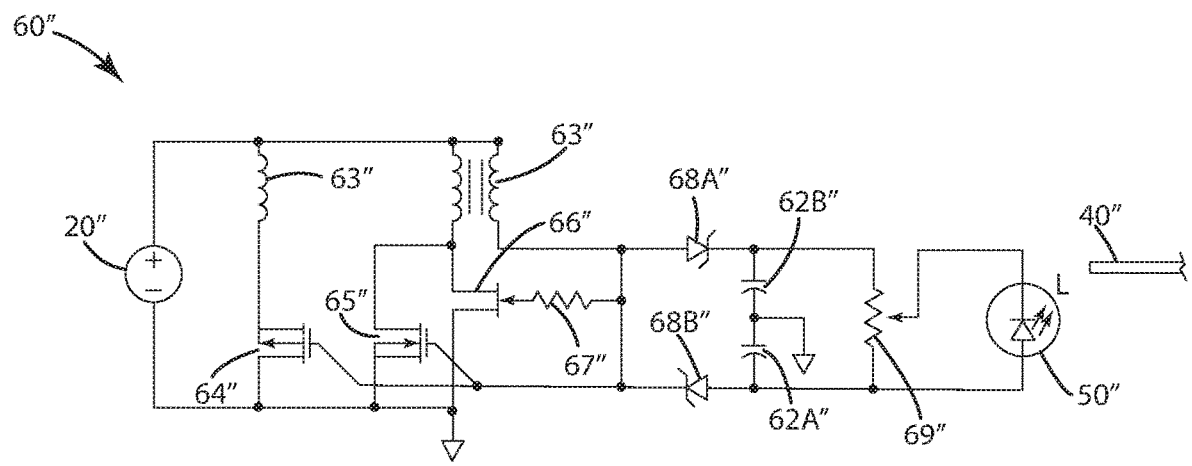
FIG. 10 is a diagram of another alternative circuit for use with the aiming device.

Yet another example of the circuit is shown in FIG. 10. There, the circuit 60" includes a thermoelectric module 20". The circuit also includes a transformer 63" which can include a transformer itself and a second primary side of a transformer. The circuit also can include a P channel enhanced MOSFET 64" and an N channel enhanced MOSFET 65". Downstream, a depletion N channel JFET 66" is included in the circuit. A gate resistor 67" is in electrical communication with the depletion N channel JFET. Diodes 68A" and 68B" are also disposed in the circuit. Capacitors 62A" and 62B" are included to store the power generated by the thermoelectric module 20". A ground can be included in this sub-circuit. The circuit 60" also can include a potentiometer 69" which can be used to modulate the intensity of light emitted from the light source 50. As illustrated, the light source 50 included in the circuit 50" can emit light L to the sight element 40". As explained above, the various components of the circuits described herein can be modified to provide different functionality and/or to accommodate different light sources or power sources as well as different thermoelectric modules.

Figure 8A:
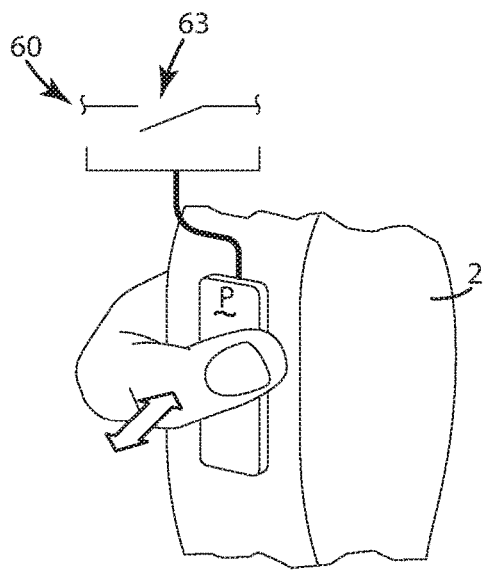
FIG. 8A is a view of a switch included in the circuit for use with the aiming device.

As mentioned above, the circuit 60, or any other circuit described herein, can include an on/off switch 63. The switch 63 can be in the form of various switches, for example, toggle switches, push button switches, pressure switches and the like. As shown in FIG. 8A, the switch 63 can be in the form of a pressure switch P that is mounted to a support structure 2 of the archery bow or projectile shooting device. The pressure switch can be a conventional pressure switch actuated by a user depressing the pressure switch P to close and/or open the switch 63 within the circuit 60. This type of on/off switch 63 can be utilized in conjunction with capacitors and/or a battery. As an example, the thermoelectric module 20 can be used to generate electricity and/or voltage. That voltage and/or electricity can be stored in the capacitor 62 or a battery, as shown in FIG. 8. The user can effectively "charge" the capacitor while waiting for a target. For example, while sitting on stand, a bow hunter can grip the hand grip, transfer the user's thermal energy to the thermoelectric module, which is then stored in the capacitor 62. When game or a target comes within the field of view of the user at a later time, the electricity stored in the capacitor and/or battery can be utilized by switching the switch 63 to the on position, such as by depressing the pressure switch P as shown in FIG. 8A. This in turn causes the light source 50 to illuminate at that time, thereby illuminating or generating light for use by the sight element. Optionally, an additional switching circuit that can stop the flow of electricity or voltage through the circuit thereby turn the light source 50 off until needed, can be provided if the capacitor 62 cannot store sufficient power.

Operation of the aiming device 10 in conjunction with the projectile shooting device in the form of the archery bow 1 shown in FIGS. 1-5 will now be described in further detail. In general, the thermoelectric module 20 is mounted in a location relative to the support structure 2 of the archery bow 1 sufficient to transfer thermal energy from a user's body U. As an example, the thermoelectric module 20 is placed in the grip area, in particular a hand grip 31 of the archery bow. When a user engages the grip area, thermal energy is transferred from the user's appendage to the thermoelectric module 20. A thermal gradient also is created between the user's appendage and/or generally the user's body heat and the colder support structure 20, for example, a riser. This thermal gradient generates electricity, current and/or voltage within the thermoelectric module.

The electricity, current and/or voltage, hereinafter referred to as electricity, is transferred via an electrical coupling element 22 to the circuit 60 shown in FIG. 8. There, the electricity flows in the direction of arrow CF to a capacitor 62, or optionally a battery, rechargeable or otherwise. The capacitor can store electricity until the switch 63 is altered from the off position to the on position. This altering can be performed via a user depressing pressure switch P as shown in FIG. 8A to close the switch 63, thereby allowing the current to flow to the remainder of the circuit 60, ultimately to the light source 50.

Upon the light source illuminating, it transfers light L as shown in FIG. 1 to an end 40E1 of the sight element 40, thereby transferring light to the end 40E2. In the embodiments shown, the illuminating end 40E2 of the sight element 40 is disposed directly in the field of view FOV. A user can align the sight element 40 with a target T as shown in FIG. 1. Upon satisfactory alignment, the user U can release the bowstring 4 of the archery bow 1 thereby propelling the arrow A toward the target. Optionally, the user can selectively choose to illuminate or not illuminate the sight element, depending on the ambient lighting conditions or other factors. Again, this can be accomplished via actuation of the switch in the circuit 60 shown in FIGS. 8 and 8A.

Optionally, when the thermoelectric module generates the electricity, the electricity is communicated to the capacitor 62. The capacitor is charged with electricity generated by the thermoelectric module. The electricity can be stored in the capacitor 62 until the user actuates the pressure switch P, turning the switch 63 in the circuit to the on position to transmit electricity to the light source 50.

Where other circuits are utilized, such as those shown in FIG. 9 or 10, the electricity and voltage provided to the light source can be modulated and/or boosted with the respective voltage boosters and/or light intensity modulators described above.

A method of shooting the archery bow 1 or generally the projectile shooting device, such as a firearm, in general is also provided. In the method, the user takes up the archery bow and transfers thermal energy from the user's body U to the thermoelectric module 20. Electricity is generated with the thermoelectric module 20 due to thermal gradient produced via the thermal energy in the user's body. More particularly, the thermal gradient is produced between the user's body and the support structure 2 of the archery bow 1. The support structure 2 acts as a heat sink for the thermal energy generated by the user's body which again operates as a heat source. In turn, this causes the thermoelectric module 20 to generate electricity.

The electricity is communicated through any of the circuits described herein ultimately to power the light source. With the light source illuminated, it in turn illuminates and/or generates light for use by a portion of the sight element so that the sight element is readily viewable in a user's field of view FOV. As noted herein, a sight element can be in the form of a fiber optic element, a reticle, a red dot element, a holographic image and/or holographic reticle, and/or other elements that assist a user in firing and aiming the projectile shooting device, for example, an archery bow 1. The user aligns the sight element with a target T and subsequently shoots an arrow A at the target. Assuming the sight element 40 is accurately aligned with the target T; the arrow will hit or impact the target T. Of course, where the projectile shooting device is a firearm, instead of shooting an arrow, the device can fire a bullet at the target.

In cases where a capacitor or battery is included in the circuit, the electricity generated by the thermoelectric module can be transferred and stored in that power source. The electricity stored in the power source can be transferred to the light source from the power source during a powering step. Alternatively, with the capacitor, battery or other power sources absent from the circuit, the thermoelectric module can directly power the light source.

In some cases, as mentioned above, the thermoelectric module and light source can serve as a backup or supplement to illuminate the sight element. For example, ambient light can be used primarily to illuminate the sight element, for example, a fiber optic element. When ambient light is sufficient to illuminate the sight element, that ambient light can be used solely by itself. Where ambient light is insufficient for adequate illumination, for example, at dusk or dawn, the thermoelectric module and light source can operate to provide the desired illumination to the sight element. Of course, if ambient light becomes sufficient to illuminate the sight element during a particular activity, the user can discontinue illuminating the sight element with the light source and thermoelectric module and return to illuminate the sight element with ambient light or some other source.

As mentioned above, the user's body generates thermal energy that is transferred to the thermoelectric module so that the thermoelectric module can generate electricity to power the aiming device. As shown in FIG. 6, an appendage of the user, specifically the user's hand UH is illustrated. There, multiple heat generating regions HR are identified. These regions are generally the warmest or hottest parts of the hand. Accordingly, a particular grip area of a projectile shooting device can be configured so that the thermoelectric module is placed in close proximity to the heat regions HR. Examples of such placement are further illustrated with the description of the firearms in the embodiments below, where the projectile shooting devices are in the form of firearms. It also has been discovered that the thermal energy generated from a user's face UF as shown in FIG. 7 can be significant enough to create a sufficient thermal gradient and operate the thermoelectric module. As shown there, the user's face includes heat regions HR which are generally aligned with the cheeks of the user's face. Thus, a projectile shooting device, when in the form of a firearm, can include a stock or other cheek piece in which the thermoelectric module is disposed. This can place a thermoelectric module in close proximity to those heat regions HR when a user is shooting and/or aiming the firearm.

Although described in connection with an archery bow being a projectile shooting device, the aiming device of the current embodiments can be made and used in a similar manner in connection with firearms.

Figure 11:
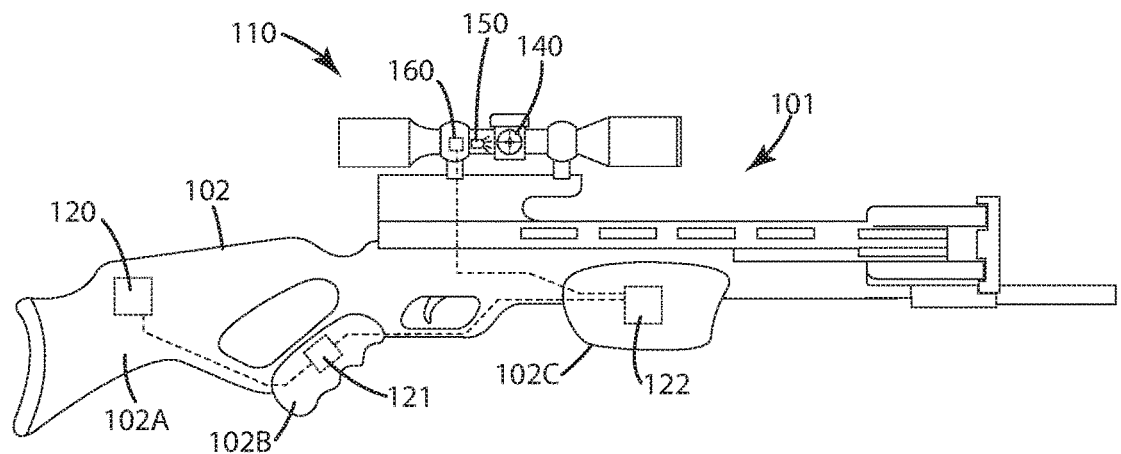
FIG. 11 is a side view of a projectile shooting device, namely a crossbow, including a first alternative embodiment of the aiming device.

A first alternative embodiment of an aiming device associated with projectile shooting device, namely a crossbow, is illustrated in FIG. 11 and generally designated 110. This embodiment is similar in structure, function and operation to the other embodiments described herein with a few exceptions. For example, the aiming device 110 is in the form of a rifle or crossbow scope mounted on crossbow 101. The scope can include an internal sight element 140 which can be in the form of a reticle. The scope can also house a light source 150 and a respective circuit 160, similar to the light source and circuits described above, except housed or otherwise associated with the scope directly. As shown in FIG. 11, there can be one or more thermoelectric modules 120, 121 and 122 arranged in different locations on the support structure, for example, the stock 102 of the crossbow. The stock 102 generally includes a butt stock 102A, a hand grip area 102B and a fore end 102C. A first module 120 can be located in the butt stock 102, generally where the cheek of a user might engage the stock. In turn, this module can absorb thermal energy from a heat region HR of the user's face UF as shown in FIG. 7.

Another additional thermoelectric module 121 can be disposed in the hand grip 102B. This thermoelectric module 121 can absorb thermal energy from one of the user's hands. Yet another thermoelectric module 122 can be disposed in the fore end 102C of the stock 102. This thermoelectric module 122 can absorb heat from another hand of the user when supporting the crossbow in the shooting position 101. As illustrated, the thermoelectric modules 120, 121 and 122 can be daisy chained together in series. These thermoelectric modules thereby each create electricity that is transferred to the circuit 160 and utilized to power the light source, thereby illuminating the reticle 140 for the user as described in further detail below. With the modules daisy chained together in series, the voltage is increased. Optionally, the circuit 160 includes a single voltage booster circuit, if desired, to boost the voltage and adequately power the light source 150.

Although shown with multiple thermoelectric modules 120, 121 and 122, this aiming device 110 included on the crossbow 101 can be modified to include only one or two thermoelectric modules, or more than three modules, depending on the desired function of the light source and illumination of the sight element 140.

Figure 12:
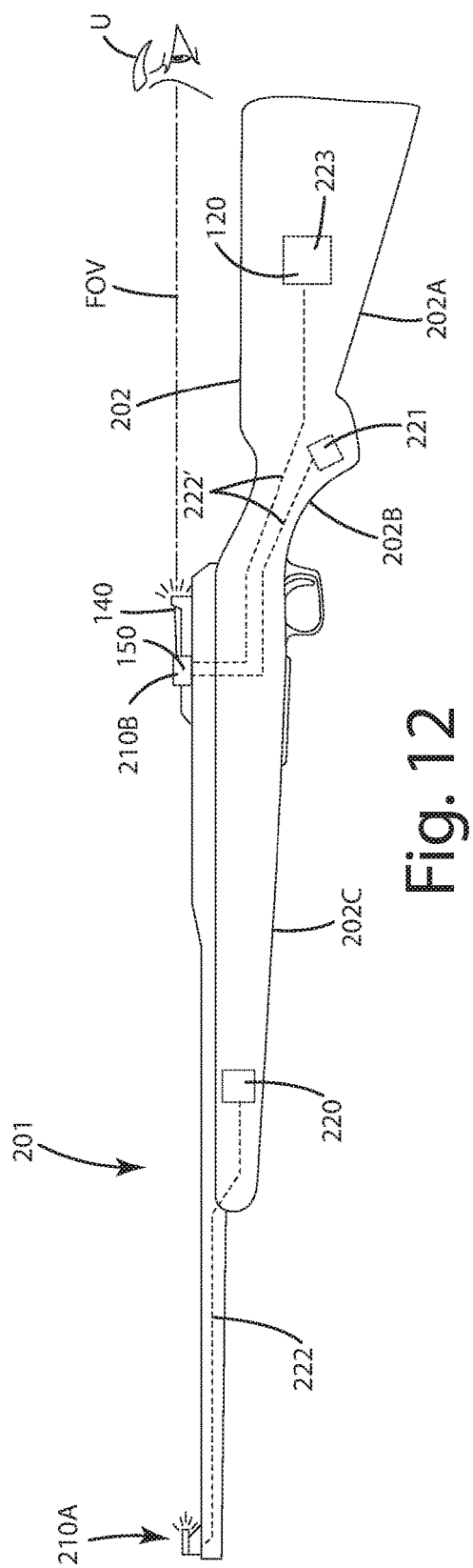
FIG. 12 is a side view of a projectile shooting device, namely a firearm, including a second alternative embodiment of the aiming device.

A second alternative embodiment of the aiming device associated with a projectile shooting device, namely a firearm, is illustrated in FIG. 12 and generally designated 210. This embodiment is similar in structure, function and operation to the other embodiments described herein with a few exceptions. For example, projectile shooting device 201 is in the form of a firearm, in particular, a rifle. The rifle includes a front aiming device 210A and a rear aiming device 210B. These front and rear aiming devices can be in the form of front and rear iron sights. The iron sights optionally can include sight elements 140 in the form of fiber optic elements that are visible to a user U, in the user's field of view FOV. The aiming devices 210A and 210B can be similar in structure, function and operation to the aiming devices of the embodiments described above with a few exceptions. Each of the aiming devices 210A and 210B can include a light source, a circuit and a sight element, for example, a fiber optic element. The front aiming device 210A, and in particular its sight element, can be illuminated with a light source that is powered by electricity generated from a thermoelectric module 220 mounted in the fore end of the stock 202C. This module 220 can be in electrical communication with the light source via an electrical coupling element 222. Optionally, the support structure 202, shown as a stock, and in particular, the fore end 202C can include one or more recesses within which the electrical connector element 222 is disposed. Indeed, a portion of the barrel of the firearm 202 can define a recess within which the electrical connector element 222 is disposed. The rear aiming device 210B can be separately powered from the front aiming device 210A, and can be distal from the front aiming device 210A. The rear aiming device 210B, and in particular, the light source 150 thereof can be in electrical communication with the thermoelectric modules 221 and 223 mounted in the pistol grip 202B and butt stock 202A of the stock 202. This is accomplished via electrical connector elements 222', which can be in the form of wires similar to the electrical connector element 222 in the front of the firearm. These thermoelectric modules can transmit electricity to the light source to illuminate the sight element 140, in a manner similar to the thermoelectric modules of the embodiments above. The thermoelectric modules 221 and 223 of this embodiment, however, can be arranged in parallel. In turn, the amperage generated by the thermoelectric modules is increased relative to a single module. When in this parallel configuration, each of the respective modules 221 and 222 can be associated with a voltage booster circuit (not shown) in a circuit of the aiming device 210B.

Optionally, although shown as including separate aiming devices 210A and 210B, with separate, isolated thermoelectric modules 220, 221 and 223, the firearm 201 can be outfitted to include a fiber optic element extending from the rear aiming device 210B to the front aiming device 210A. This fiber optic element can extend along the barrel, optionally within a recess or otherwise under a cover, protected from the environment, up to the front sight of the firearm. The fiber optic element can be disposed in the front sight so that it is visible to a user U and within their field of view FOV when aiming or shooting the firearm. In this manner, the front fiber optic sight element can be illuminated by a light source 150 within or associated with the rear sight 210B. Accordingly, a front thermoelectric module 220 and associated wiring 222 can be absent from the construction. Of course, this construction can be reversed, so the front aiming device includes a light source that also illuminates the rear fiber optic sight element.

As will be appreciated, when utilizing fiber optics to transmit illumination from a light source in one location on a projectile shooting device to another location, those fiber optics can be protected in various ways. In some instances, they can be coated with a special coating to prevent them from cracking or breaking. The elements can be adhered to the exterior of the firearm. In other instances, components of the firearm, such as a stock, barrel, slide, receiver, rail or other component, can include a groove, recess or channel—or even an internal tube or cavity. The fiber optic element can be disposed through the same. These elements can be formed in the firearm when its components are initially constructed. For example, a slide or barrel can include a recess formed directly in the metal when the same is constructed. With a polymer stock, a recess or groove can be formed directly in the stock when it is molded from a polymer. Where a stock is constructed from wood, the groove or recess can be artfully produced in the wood.

Figure 13:
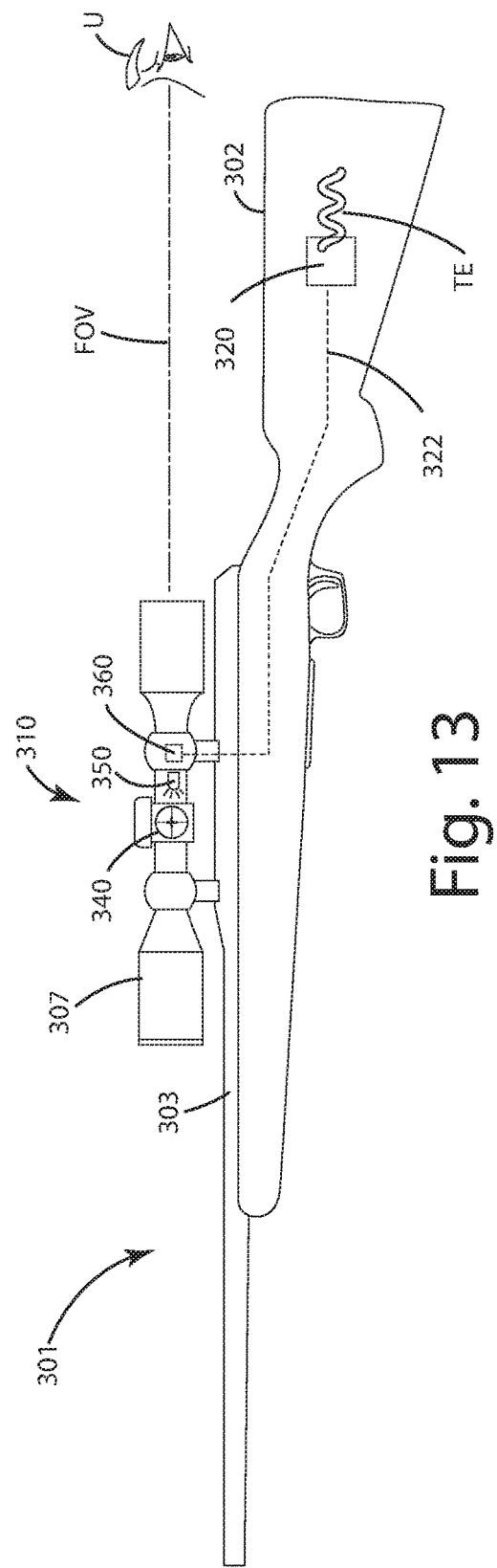
FIG. 13 is a side view of a projectile shooting device, namely a firearm, including a third alternative embodiment of the aiming device in the form of a rifle scope.
Figure 19:
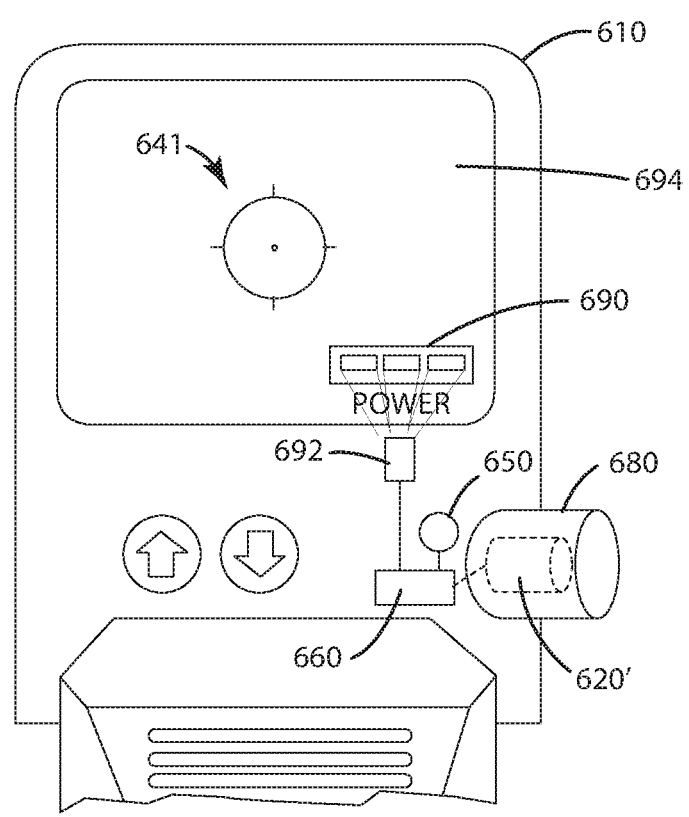
FIG. 19 is a schematic illustrating the sixth alternative embodiment of the aiming device of FIG. 18 from the perspective of a user when the firearm is in a shooting position.

A third alternative embodiment of an aiming device is illustrated in FIGS. 13 and 19 and generally designated 310. This embodiment is similar in structure, function and operation to the other embodiments described herein with a few exceptions. For example, the projectile shooting device in this construction also can be a firearm 301 in the form of a rifle. The rifle includes a barrel and a stock 302 attached thereto. The aiming device 310 is in the form of a scope including a sight element 340 in the form of a reticle, mounted in the within a rifle scope tube 307. The rifle scope tube can include conventional lenses, glass and other prism type magnifiers. It also can be constructed to be of a variable objective and can have one or more magnification settings if desired.

Generally, the aiming device 310 can be mounted to a support structure such as the barrel 303 or receiver. The aiming device can include a light source 350, which can be associated with a circuit 360. The circuit can be in electrical communication with a thermoelectric module 320 disposed in the stock 302 and/or other locations described in connection with the other embodiments herein. The thermoelectric module can be in electrical communication with the light source 350 via an electrical connector element 322 like those described in other embodiments herein. The module 320 can be placed in a location sufficient to absorb thermal energy TE from a user's body when the rifle is brought to a shooting position or into a field of view FOV of a user U.

Figure 14:
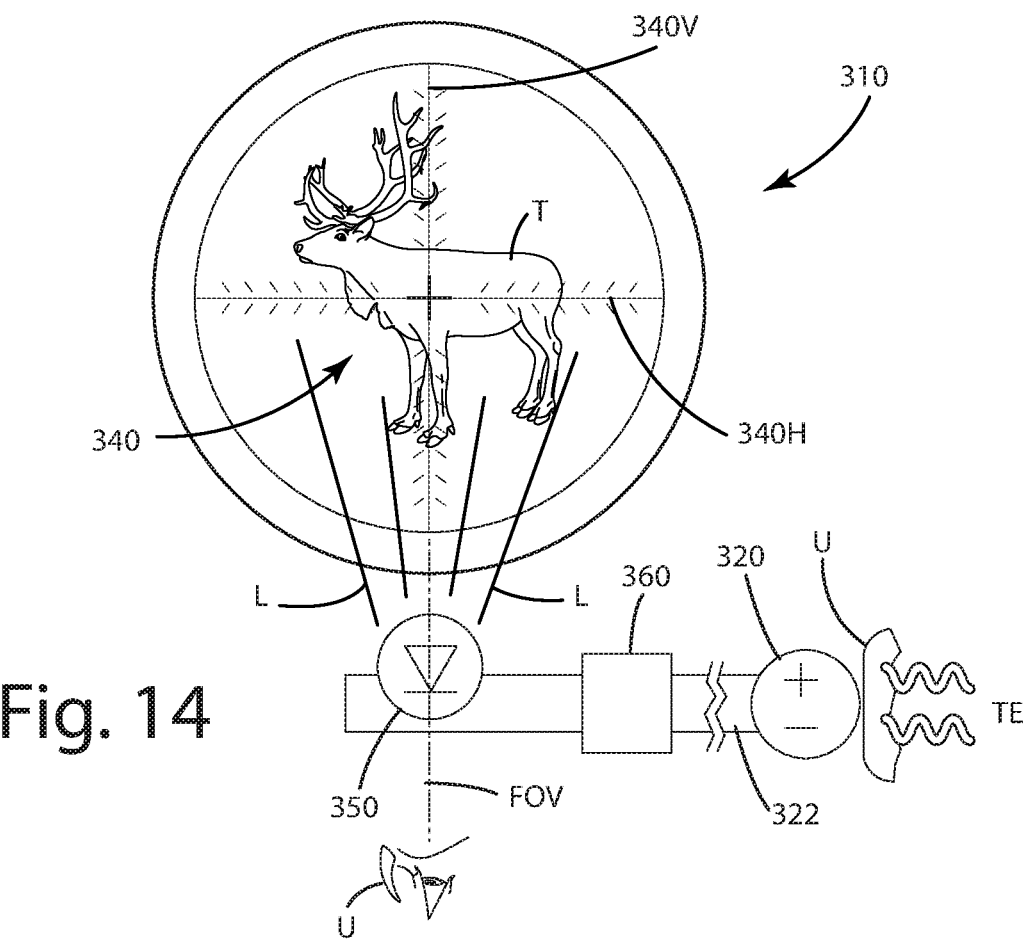
FIG. 14 is a schematic illustrating of the third alternative aiming device of FIG. 13 from a perspective of a user when the firearm is in a shooting position.

As shown in FIG. 14, the sight element 340 is in the form of a reticle having a vertical crosshair 340V and a horizontal crosshair 340H. The intersection of these crosshairs provides a point of aim. This point of aim can be aligned with a target so that the rifle 301 can be fired at the target, and assuming the aiming device is properly sighted in, the bullet will hit the target.

The reticle, and in particular the crosshairs are illuminated by the light source 350. The crosshairs 340V and 340H optionally can be coated with a special light absorbing or reflecting coating or material so that when the light from the light source 350 illuminates them, the crosshairs become illuminated or generally more visible, particularly in low ambient light conditions.

Optionally, as illustrated in FIG. 14, the light source 350 can be associated with a circuit 360 which can be in the form of any of the circuits described in any of the embodiments herein. This circuit and/or the light source 350 is in electrical communication with the thermoelectric module 320 which can absorb thermal energy TE from a user's body.

Figure 15:
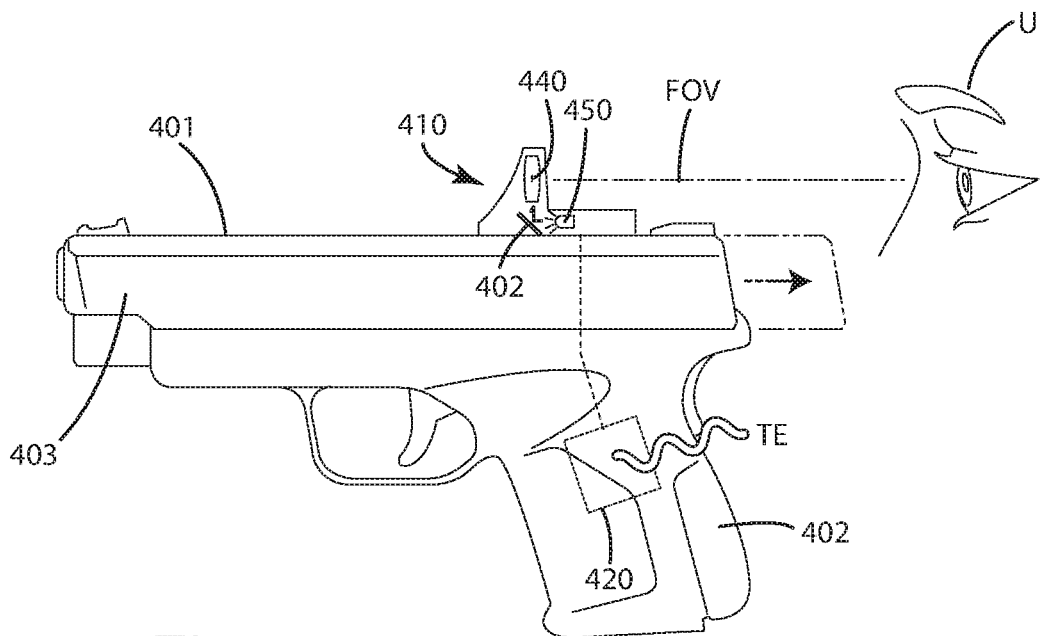
FIG. 15 is a side view of a projectile shooting device, namely a firearm, including a fourth alternative embodiment of the aiming device in the form of a red dot scope.
Figure 16:
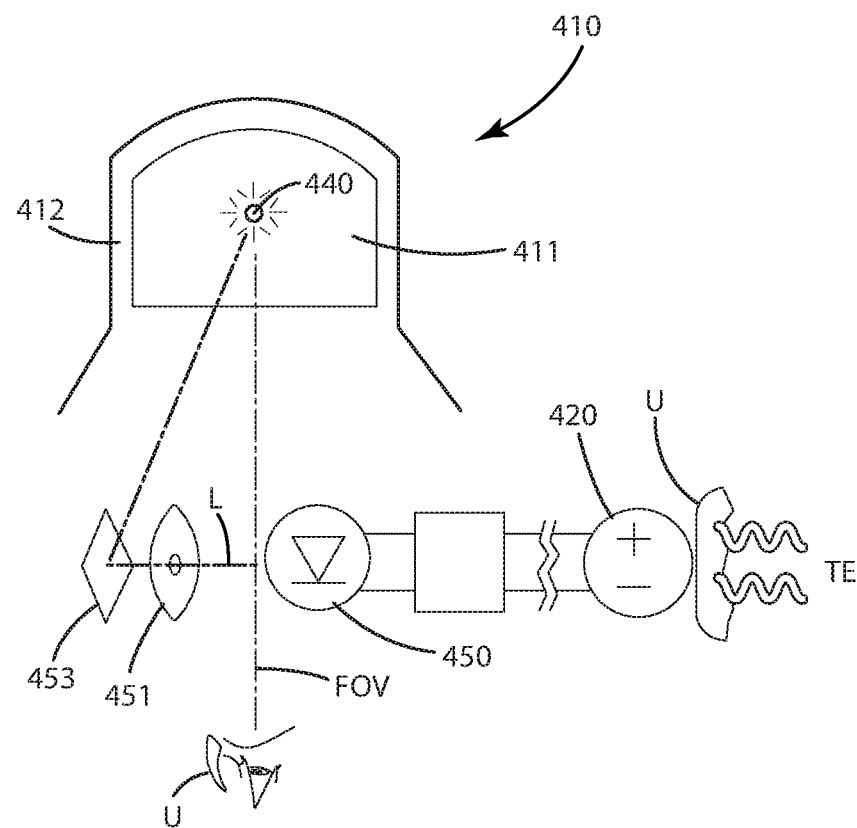
FIG. 16 is a schematic illustrating the fourth alternative embodiment of the aiming device of FIG. 15 from the perspective of a user when the firearm is in a shooting position.

A fourth alternative embodiment of the aiming device associated with a projectile shooting device, in the form of a semiautomatic pistol, is illustrated in FIGS. 15 and 16 and generally designated 410. This embodiment is similar in structure, function and operation to the other embodiments described herein with a few exceptions. For example, the device 401 is in the form of a pistol having a grip 402 and a slide 403. When the pistol is fired, the slide 403 slides rearward as shown in broken lines. Thus, the aiming device 410 mounted to the slide 403 also moves. The aiming device 410 can be in the form of a red dot scope which includes a red dot sight element 440. As used herein, the term red dot scopes also encompass reflex sights, which generally have the same structure and operate similar to red dot scopes. The sight element is a reflection of a light on a transparent or clear lens 411 disposed in a housing 412. In this embodiment, the sight element 440 can be considered the reflected light or dot that is displayed on the lens 411 or otherwise projected onto a viewing plane or surface. Generally, this sight element or red dot 440 is illuminated or created by the light source 450. More particularly, the light source projects illumination or light toward a plate 451. The plate includes one or more apertures 452. Only the light that goes through the aperture passes by plate 451. This light can be in the form of a small red, green or other colored dot depending on the color of the light source 450 projected on a viewing plane or surface. This dot is a reflected off of a mirror 453, and projected on the lens 411 within the field of view FOV of the user U as shown in FIG. 16. In the same manner as described above, the light source 450 can be powered directly or indirectly by the thermoelectric module 420, and in particular, by the thermal energy TE produced by the user U. Further optionally, the red dot can be substituted with any reticle typically used with projectile shooting devices such as firearms. In some cases, the substitute reticle can include multiple crosshairs to compensate for bullet drop. In other cases, the reticle can be a fast acquisition reticle; such as a circle or polygon, or a ballistic compensation reticle, a mil-dot reticle, and/or a ranging reticle. Any variety of reticle patterns is contemplated for use herein.

Optionally, the lens and certain other components of the red dot scope, also referred to as a reflex scope, can be modified from the optical sight disclosed in U.S. Pat. No. 8,443,541, entitled Optical Sight, which is hereby incorporated by reference in its entirety.

Although shown as a single dot sight element 440, the sight element of the aiming device 410 can be modified to be of virtually any appearance. For example, multiple dots can be aligned in a vertical line above one another on the lens 411. Alternatively, other types of dot or reticle configurations can be implemented directly on the lens 411. This can be accomplished by altering the shape and configuration of the aperture 452 of the plate 451 so that certain illumination patterns are generated by the light passing through specifically configured apertures.

Further optionally, the aiming device described herein can be used in systems that are not mounted to a projectile shooting device. For example certain types of red dot sight elements are used in conjunction with a finder's scope used in connection with photography (camera) or astronomy (telescope) conventional telescope. These types of red dot scopes are standalone units, and are not used as sighting devices for projectile shooting devices. Indeed, most of these scopes are either mounted directed to a camera, telescope and/or tripod. Again, these scopes can include all the elements and can function the same as the aiming device, for example, which is similar to a red dot scope used on a firearm, however, these devices simply are not mounted on a firearm or other projectile shooting device. Likewise, the other types of aiming devices described herein can also be utilized in conjunction with devices other than projectile shooting devices, such as cameras, telescopes or other long range viewing instruments.

Figure 17:
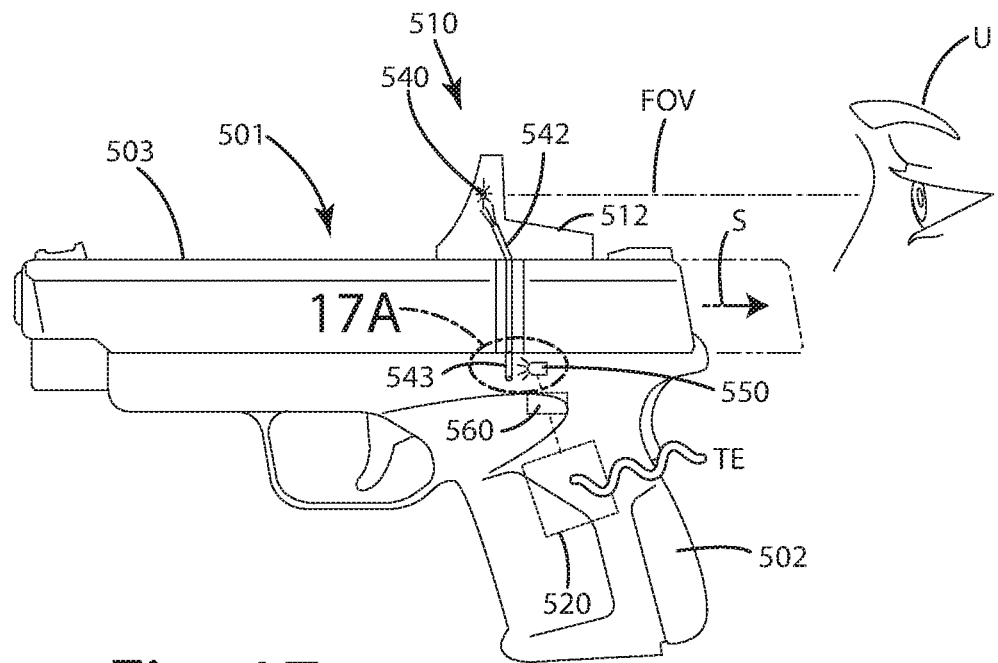
FIG. 17 is a side view of a projectile shooting device, namely a firearm, including a fifth alternative of the aiming device.
Figure 17A:
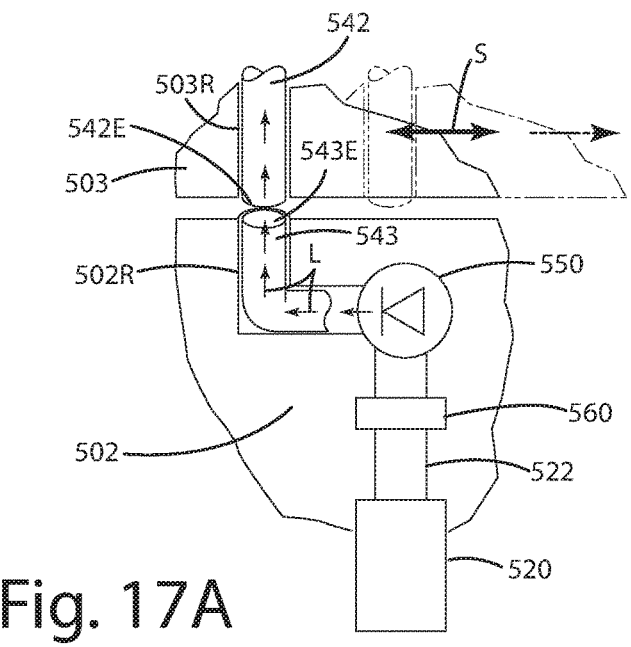
FIG. 17A is a close-up view of fiber optic elements taken from 17A of FIG. 17.

A fifth alternative embodiment of the aiming device associated with a projectile shooting device, in the form of a semiautomatic pistol, is illustrated in FIGS. 17 and 17A and generally designated 510. This embodiment is similar in structure, function and operation to the other embodiments described herein with a few exceptions. For example, this construction includes an aiming device 510 generally in the form of a red dot scope. The red dot scope, however, is operated via a fiber optic element that is generally disposed within the housing 512 of the aiming device 510. The sight element 540 itself is in the form of a dot or point that is reflected or otherwise projected onto a lens similar to that described above in connection with the lens 411 in the embodiment immediately above. This dot, however, is projected via the first fiber optic element 542 pointing at the lens. This fiber optic element 542 can be aimed toward the lens of the aiming device so that a small dot is within the field of view FOV of the user when illuminated.

The fiber optic 542 can extend out of the housing 512 and can be located within a recess 503R of the slide 503. The slide 503, as mentioned above, slides back and forth upon firing of a round. The sliding action feeds another round into a chamber, and thus the barrel of the firearm 501. The direction of movement is generally indicated by the arrows S depicted in FIGS. 17 and 17A. To account for this sliding movement and still transmit illumination with the fiber optic element 442, a chain of fiber optic elements that transmit illumination from one fiber optic element to another without direct contact is utilized.

As shown more particularly in FIG. 17A, the thermoelectric module 520, circuitry 560 and light source 550 can be disposed in the support structure 502, for example, the frame or hand grip of the firearm 501. The thermoelectric module operates off a thermal gradient generated by the user grasping the firearm to illuminate the light source 550. However, in this embodiment, a second fiber optic element 543, physically separated from the first fiber element 542 that extends up into the housing 512 of the aiming device 510, is mounted in proximity to the light source 550. In operation, light L from the light source 550 is projected on an end of the second fiber optic 543. The light as shown in arrows is transmitted through the second fiber optic element 543 to the end 543E of the second fiber optic element 543. When the end 542E of the first fiber optic element 542 is placed adjacent or generally aligned with the end 543E of the second fiber optic element 543, light transmitted out of the end 543E is transmitted directly to the end 542E of the fiber optic element 542. The light is conveyed through the element 542 and projected as sight element 540 within the aiming device.

Generally the ends 542E and 543E are aligned when the slide is stationary, that is, when a round is not being fired from the firearm as illustrated in FIG. 17A. However, when the round is fired, the slide 503 slides rearward in direction S. Upon sliding, the ends 542E and 543E are no longer aligned, thus even though the light source illuminates the secondary fiber optic element 543, that light is not transmitted to the fiber optic element 542 until the slide returns to its normal, stationary position. Upon return to that position, as shown in FIG. 17A, light is immediately transmitted from the secondary fiber optic 543 to the fiber optic 542 to provide a sight element 540 for the user U to view within their field of view FOV. During the sliding action, the sight element 540 may be temporarily interrupted or generally disappear from the user's field of view FOV because light is no longer being transmitted through the fiber optic element 542. Typically this is of little consequence because the firearm is slightly recoiling and the user cannot fully view the aiming device 510 anyway.

Of course, if desired, the second fiber optic element 543 can be duplicated so that the sight element 540 is always visible, as long as the light source 550 is on. For example, multiple additional second fiber optic elements (not shown) can be placed behind the fiber optic element 543 illustrated by the light source 550. During the rearward sliding of the slide in direction S at any one time, at least one of these additional second fiber optic elements can be aligned with the fiber optic element 542.

Optionally, given the debris, powder residue and other environmental features that the firearm 501 may encounter, the fiber optic elements 542 and 543 as illustrated can be disposed within recesses 503R and 502R, respectively. These recesses can further be covered, sealed or otherwise protected to protect the fiber optic elements therein. Further, although shown in conjunction with a semiautomatic pistol, the construction and multicomponent fiber optics used in this embodiment are well suited for semiautomatic rifles or other firearms including a slide or moving component upon which the aiming device is typically mounted.

Figure 18:
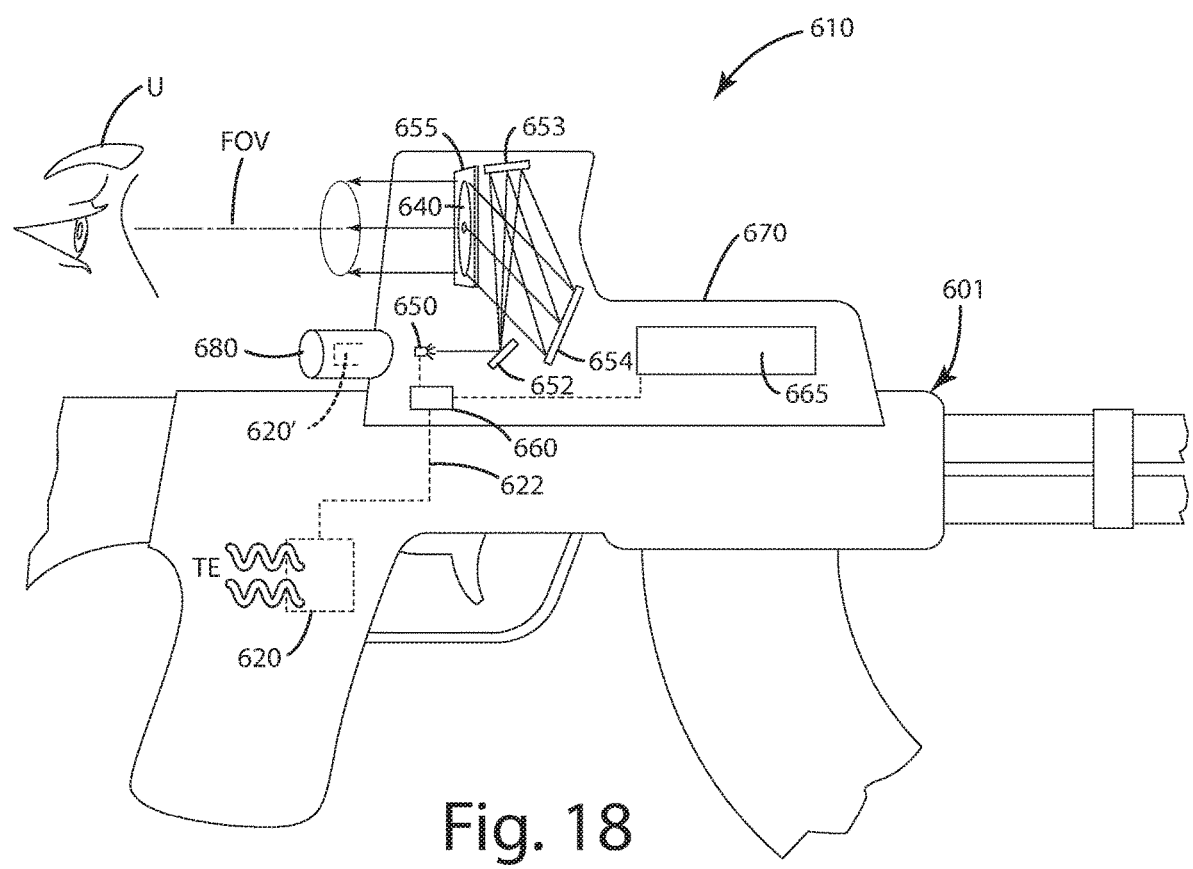
FIG. 18 is a side view of a projectile shooting device, namely a firearm, including a sixth alternative of the aiming device.

A sixth alternative embodiment of an aiming device associated with a projectile shooting device, in the form of a carbine, is illustrated in FIGS. 18 and 19 and generally designated 610. This embodiment is similar in structure, function and operation to the other embodiments described above herein with a few exceptions. For example, this construction includes an aiming device generally in the form of a holographic weapon sight, also referred to as a holographic diffraction sight or a holo sight. In this construction, the aiming device can include a light source 650 which can be associated with a circuit 660. This circuit can be in electrical communication with a thermoelectric module 620 disposed in the grip area and/or other locations described in connection with the other embodiments herein. The thermoelectric module 620 can be in electrical communication with light source 650 via an electrical connector element 622 like those described in the other embodiments herein. The module 620 can be placed in a location sufficient to absorb thermal energy TE from a user's body when the firearm is brought to a shooting positing or into a field of view of the user.

The light source 650 can be in the form of a laser diode, also commonly referred to as a laser. The sight element 640 in this case can be the reticle image hologram 640 recorded or disposed within the substrate 655 that is ultimately illuminated by the light from the light source 650 and subsequently creates the holographic image 641 which is superimposed on the field of view FOV. This reticle image hologram can be superimposed or displayed in the form of a desired image reticle or other aiming indicia, in the user's field of view FOV by way of a laser transmission hologram. Generally, the laser transmission hologram is a reticle image hologram 640 that is recorded in a substrate 655 or some other three dimensional space. The recorded hologram 640, or sight element, in the substrate 655 is illuminated via the light emitted by the light source/laser 650. In particular, the light source/laser diode 650 emits radiation onto a first reflector 652 which is transmitted to and reflected to a collimating reflector 653. The light thereafter reflects toward a holographic grating 654, and is then transmitted through the substrate 655, thereby illuminating the hologram/sight element 640 and creating the holographic image 641.

The aiming device 610 as illustrated can include a circuit 660 associated with the light source 650. Because the light source is a laser diode, it can require significant electricity to power it. If desired, a voltage booster as discussed in the embodiments herein, can be incorporated into the circuit. Additionally, a replaceable and/or rechargeable power source 665 such as a battery, can be included in the aiming device 610. This power source 665 and the other components of the aiming device can all be housed within a housing 670, which can withstand shock and vibration.

Optionally, the lens and certain other components of the holographic aiming device can be modified from the optical sight disclosed in U.S. Pat. No. 5,483,362 to Tai, which is hereby incorporated by reference in its entirety.

Further optionally, the light source 650 can be in communication with a circuit 660 which is further in communication with a grip area 680 in the form of a projection extending directly from the aiming device 610. Optionally, with this construction, the coupler 622 and the grip area 620 associated with the firearm 601 can be eliminated. In such a case, a user can grasp the projection 680. The projection 680 can include an internal thermoelectric module 620'. The thermoelectric module can generate electricity transferring it to the circuit 660 and the laser diode 650, thereby illuminating the laser diode.

Of course, the projection form of a grip area 680 shown in FIGS. 18 and 19 can be used in conjunction with any of the other rifle scopes, red dot scopes, fiber optic systems of the other aiming devices described in the embodiments herein. In these constructions, the thermal electric module is joined with or is associated directly with the aiming device (rather than being on the projectile shooting device, and can power the light source. Sometimes, the additional thermoelectric modules on different grip areas of the firearm, bow and or other projectile string device can be eliminated.

As shown in FIG. 19, the projection 680 can extend outwardly from at least a portion of the rear of the aiming device 610. This perspective also illustrates the projected hologram 641 within the field of view of the user. In addition, this view illustrates an optional feature for use in connection with the holographic weapon sight, which also can be used in conjunction with the red dot devices and any other electronic device used in conjunction with the thermoelectric module and concepts related thereto. Specifically, the viewing area 694 of the aiming device 610 can include a gauge 690 or other representation that is displayed within the user's field of view. This gauge can provide a visual indication of the relative power of a battery 665 and/or of electricity or current generated by the thermoelectric module 620' and generally being conveyed to or from the laser diode 650. This gauge 690 can be displayed by a small projector 692 onto the viewing area 694. Of course, in other implementations, a lower portion of the viewing area 694 can be in the form of a liquid crystal display or other visual output device that can display indicia representative of the amount of power stored by an optional battery in the aiming device, or the function of the thermoelectric module, or the input or output of electricity to the light source 650. Again, this type of power gauge and display of the same can be incorporated into any of the aiming device embodiments herein.

Further optionally, the aiming device 610 can be equipped with mechanical or electronic windage and/or elevation adjusters, so that the image hologram can be calibrated to provide accurate shooting adaptabilities. The other aiming devices of the other embodiments herein can optionally be equipped with such windage and elevation adjusters as well.

A seventh alternative embodiment is illustrated in FIGS. 20-25 and includes a range finder 710 into which a thermoelectric module 720 is incorporated. This embodiment is similar in structure, function, and operation to the other embodiments described herein with a few exceptions. For example, in addition to a light source 750, the range finder 710, includes additional components for determining and displaying a distance to an object.

Figure 21:
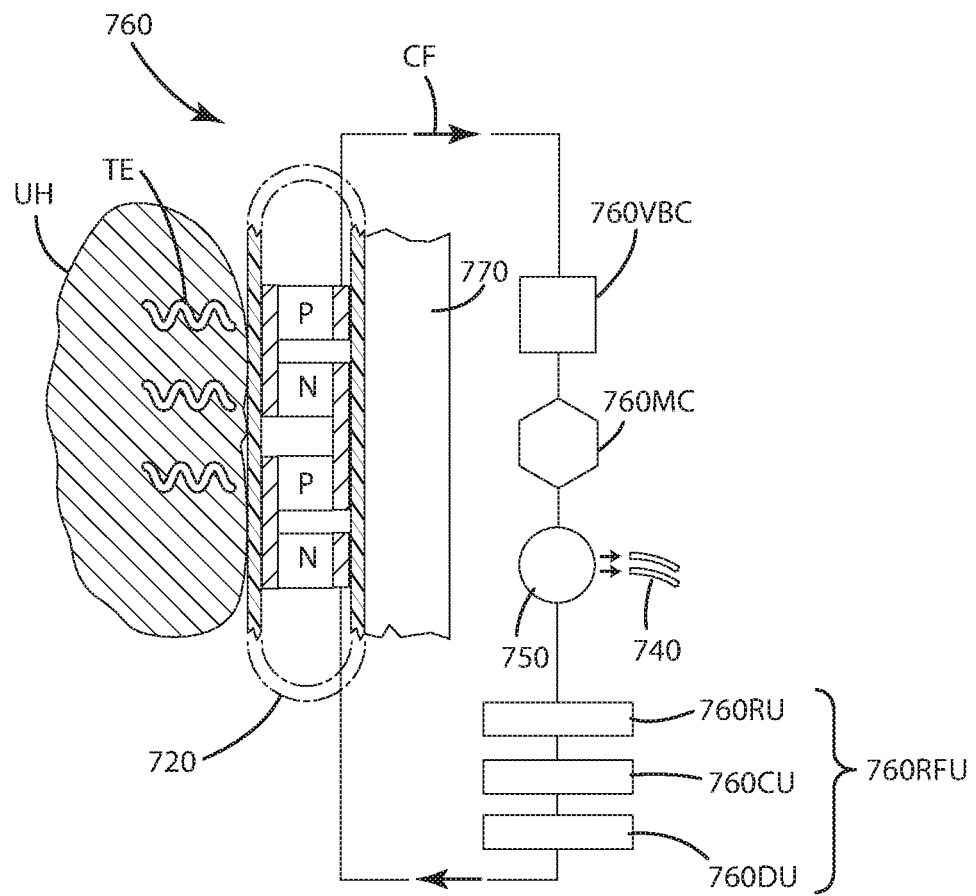
FIG. 21 is a diagram of a circuit for use with a range finder having a thermoelectric module incorporated therein.

Referring now to FIG. 21, the range finder 710 includes a circuit 760 that is similar to the circuit 60' of FIG. 9 except for the additional components relating to determining and displaying a distance to a target object. Non-limiting examples of range finders that can be used with the embodiments described herein can be found in U.S. Pat. No. 8,072,583, entitled "Range-Finding Device," issued Dec. 6, 2011; U.S. Pat. No. 8,638,423, entitled "Range Finder," issued Jan. 28, 2014; U.S. Pat. No. 8,314,923, entitled "Configurable Rangefinding Devices and Methods," issued Nov. 20, 2012; U.S. Pat. No. 8,780,333, entitled "Range Finder," issued Jul. 15, 2014; and U.S. Pub. 2016/0061567, entitled "Accessory Display for Optical Sighting Devices," published Mar. 3, 2016, all of which are incorporated herein by reference in their entirety. The circuit 760 can include any components found in a conventional range finder for determining and displaying the distance to an object. In the embodiment of FIG. 21, the circuit 760 includes a light receiving unit 760RU, a distance calculation unit 760CU, and a display unit 760DU. The light intensity modulation circuit 760MC is optional. The light source 750, light receiving unit 760RU, distance calculation unit 760CU, and display unit 760DU collectively define a range finding unit 760RFU. The circuit 760 can include additional components related to other conventional features of a range finder, non-limiting examples of which include a temperature sensing unit, a wind speed sensing unit, a compass unit, and a unit for calculating a height of the target object.

Figure 22:
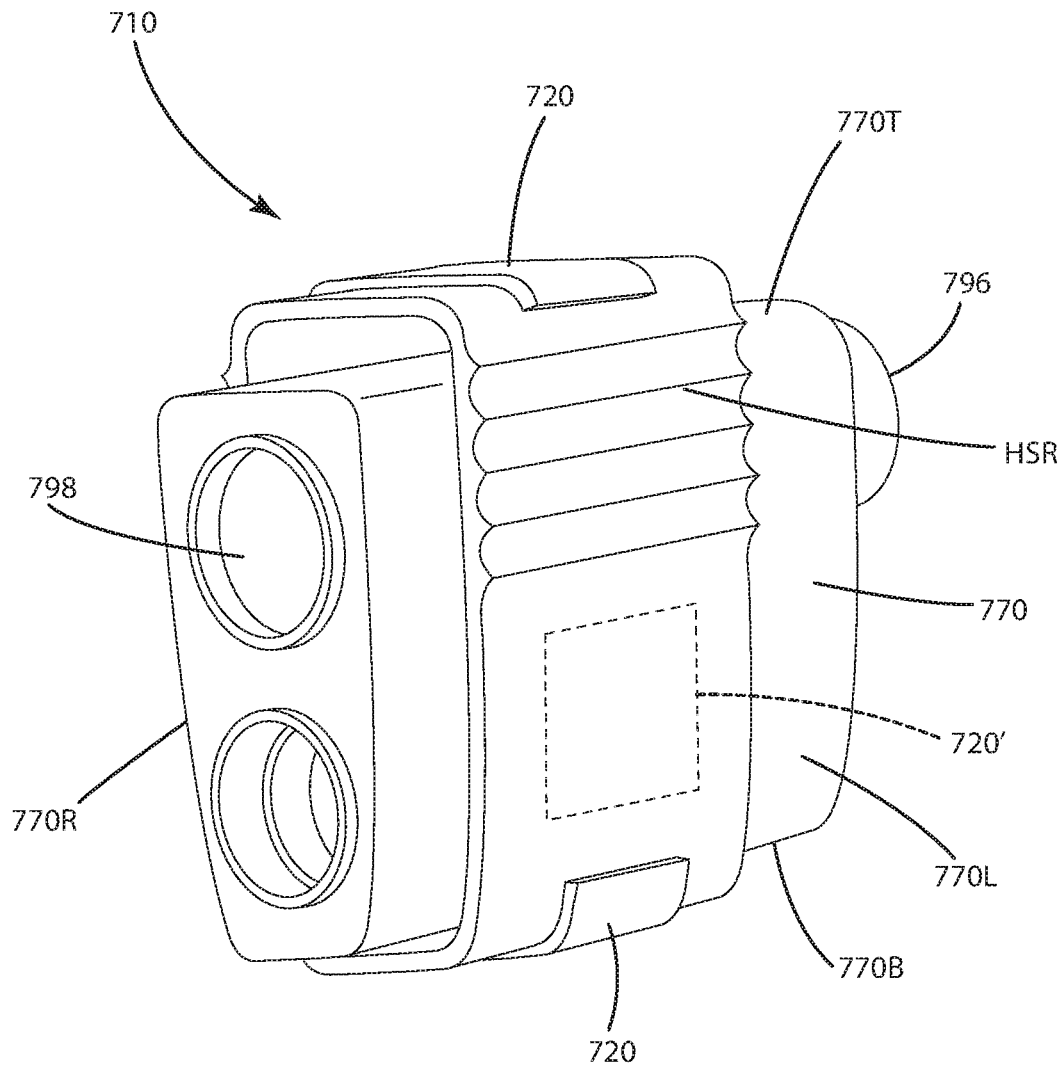
FIG. 22 is a schematic view of a range finder having a thermoelectric module incorporated therein.

The light source 750 emits light that is reflected by the target object and the light receiving unit 760RU receives the reflected light. The light source 750 may be any suitable type of laser known in the field of range finders. The distance calculation unit 760CU calculates the distance to the object based on the light received by the light receiving unit 760RU and the distance is communicated to the user by the display unit 760DU in a conventional manner. The display unit 760DU can be an electronic display that is superimposed on a field of view of the range finder 710 between an eye piece 796 and an objective 798 (FIG. 22). The display unit 760DU can display text and/or graphics relating to the distance to the target object and optionally additional information, non-limiting examples of which include a height of the object, temperature, wind speed, battery power, etc. The display unit 760DU may be in the form of an LCD panel, a fiber optic display, light emitting diodes (LEDs), or organic LEDS. Optionally, the display unit 760 can be an electronic display that is outside the field of view.

The circuit 760 is in electrical communication with the thermoelectric module 720 disposed in the grip area and/or other locations described in connection with the other embodiments herein. The thermoelectric module 620 can be in electrical communication with light source 650 and the other components 760RU, 760CU, and 760DU of the range finder 710 via an electrical connector element like those described in the other embodiments herein. The module 720 can be placed in a location sufficient to absorb thermal energy TE from a user's body during use.

Figure 20:
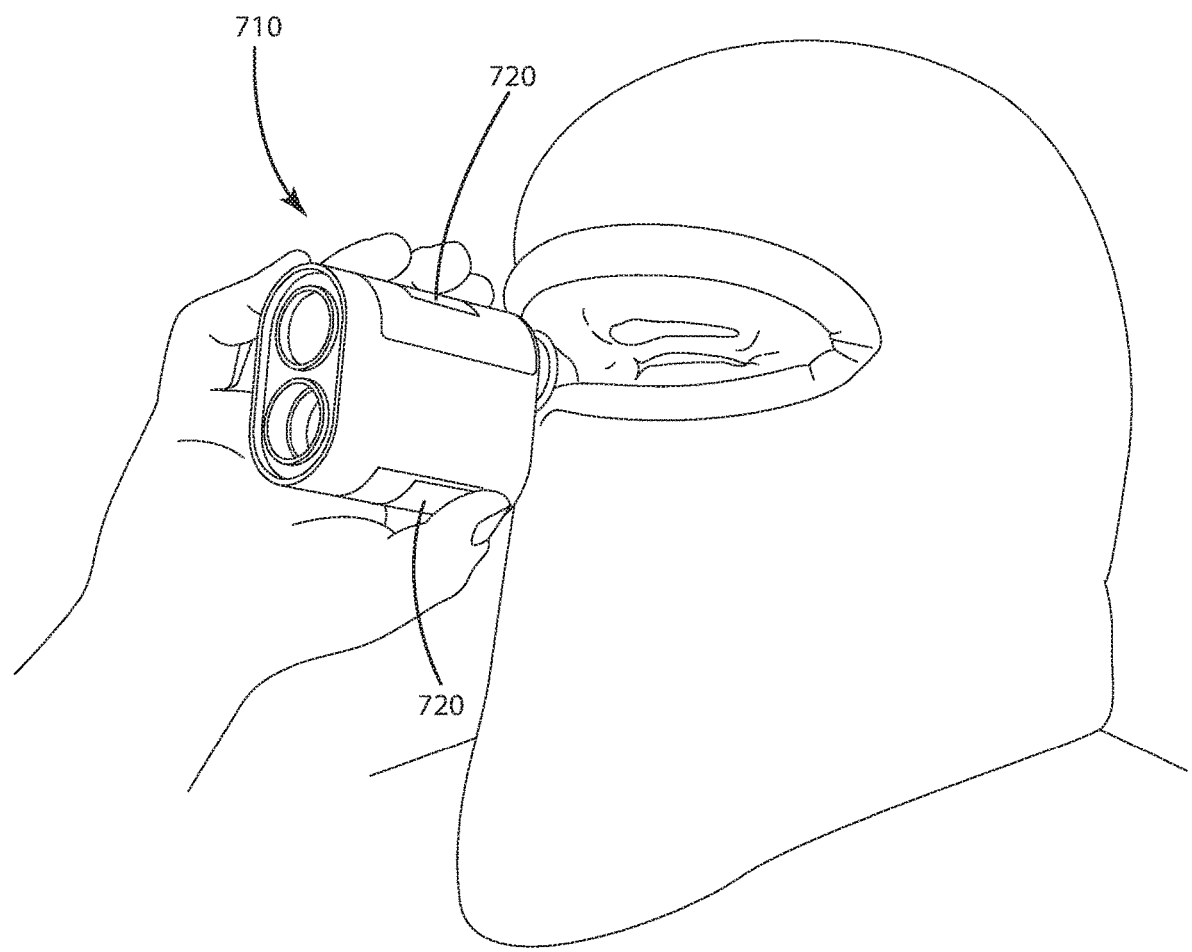
FIG. 20 is a perspective view of a range finder having a thermoelectric module incorporated therein according to a seventh alternative embodiment.
Figure 23:
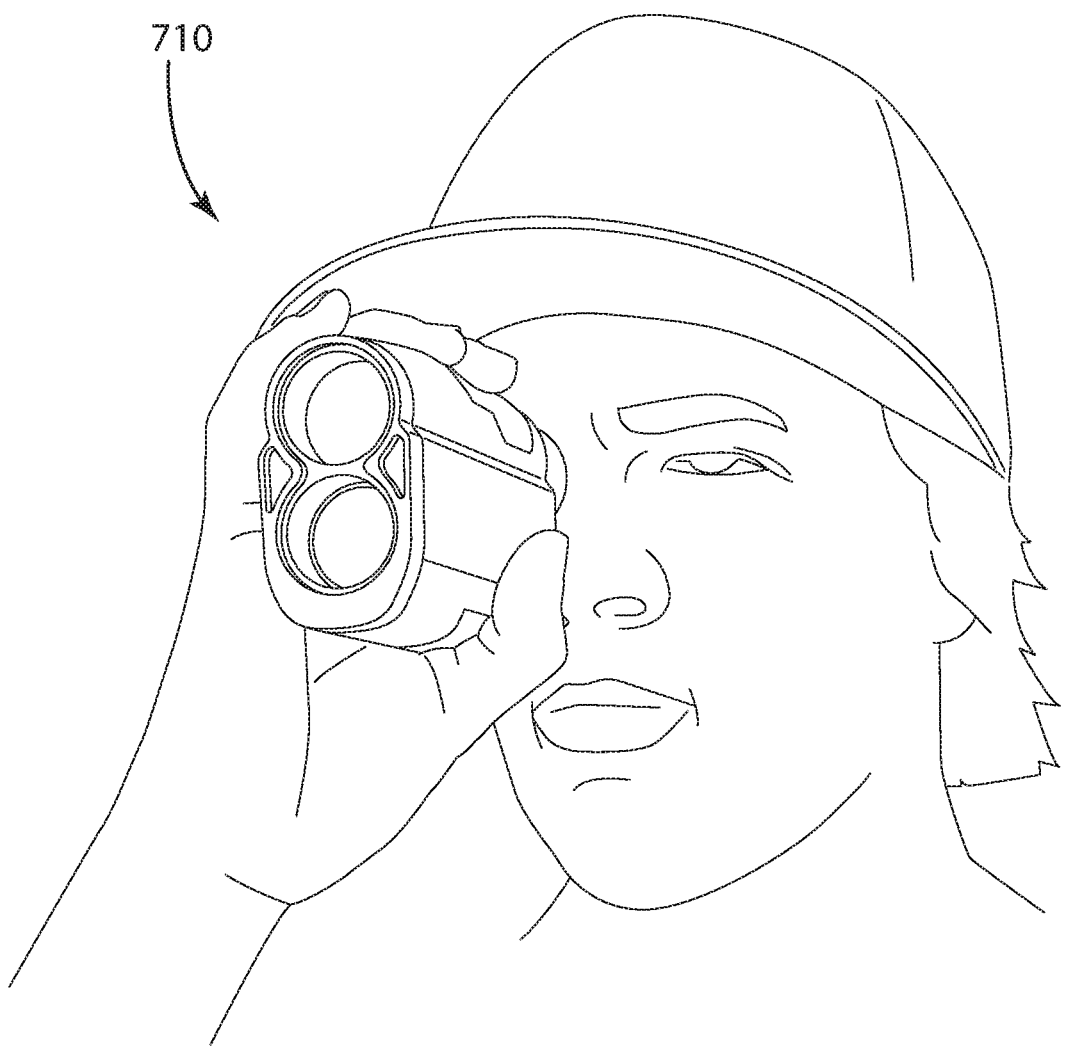
FIG. 23 is a perspective view of a range finder having a thermoelectric module incorporated therein.

Referring now to FIG. 22, the range finder 710 includes a housing 770 which incorporates the components of the range finder 710. A thermoelectric module 720 is disposed on a top 770T and a bottom 770B of the housing 770 such that a user's hand comes into contact with the thermoelectric module 720 when the range finder 710 is grasped between a user's fingers and thumb, as illustrated in FIG. 20. Optionally, a thermoelectric module 720' is disposed on one or both of the left and right sides 770L, 770R of the housing 770 such that a user's palm and/or thumb come into contact with the thermoelectric module 720' during use, as illustrated in FIG. 23. Further optionally, a thermoelectric module (not shown) is disposed on a rear surface 770R of the housing 770 adjacent the eye piece 796 for contacting a user's cheek and/or under eye area during, as shown in FIG. 23. The range finder 710 may include one or more of the thermoelectric modules 720 and 720' on the top, bottom, rear, left, and/or right sides of the housing 770 individually or in any desired combination.

As described above with respect to the thermoelectric module 20 of FIGS. 2 and 2A, the thermoelectric module includes a first surface that comes into contact with a user's body to receive thermal energy TE from the user that is converted to electrical power for use in operating the range finder 710. The thermoelectric module also includes a heat sink, also referred to as a cooler surface, which is used to generate a thermal gradient with the first surface that contacts the user's body. The heat sink in the range finder 710 may be configured in a similar way to generate a thermal gradient during use. For example, the heat sink in the range finder 710 can be configured to engage parts of the housing 770 that typically do not come into contact with the user's body during use, such as heat sink ridges HSR (also referred to as fins) disposed on the left and/or right sides 770L, 770R. Optionally, a front portion of the housing 770 adjacent the objective 798 may be utilized as a heat sink.

The range finder 710 may require anywhere from 2 to 12 Volts of electricity to operate depending on the optional features included in the range finder 710. The voltage booster 760VBC can be included in the circuit 760 to provide a voltage output from the thermoelectric module 720 in the range of about 2 to 12 Volts, optionally about 3 to 10 Volts, and further optionally about 5 to 8 Volts. Optionally, a replaceable and/or rechargeable power source, such as a battery (not shown), can be included in range finder 710 similar to the battery 665 of the aiming device 610 of FIG. 19.

The range finder 710 may be a hand-held range finder, as illustrated in FIGS. 20-25. Optionally, the range finder 710 can be mounted to a projectile shooting device, such as an archery bow or a firearm, or a support structure. Optionally, the components of the range finder 710 can be incorporated into any one of the aiming devices described herein to calculate and display the distance to a target object in addition to the sight element.

Figure 24:
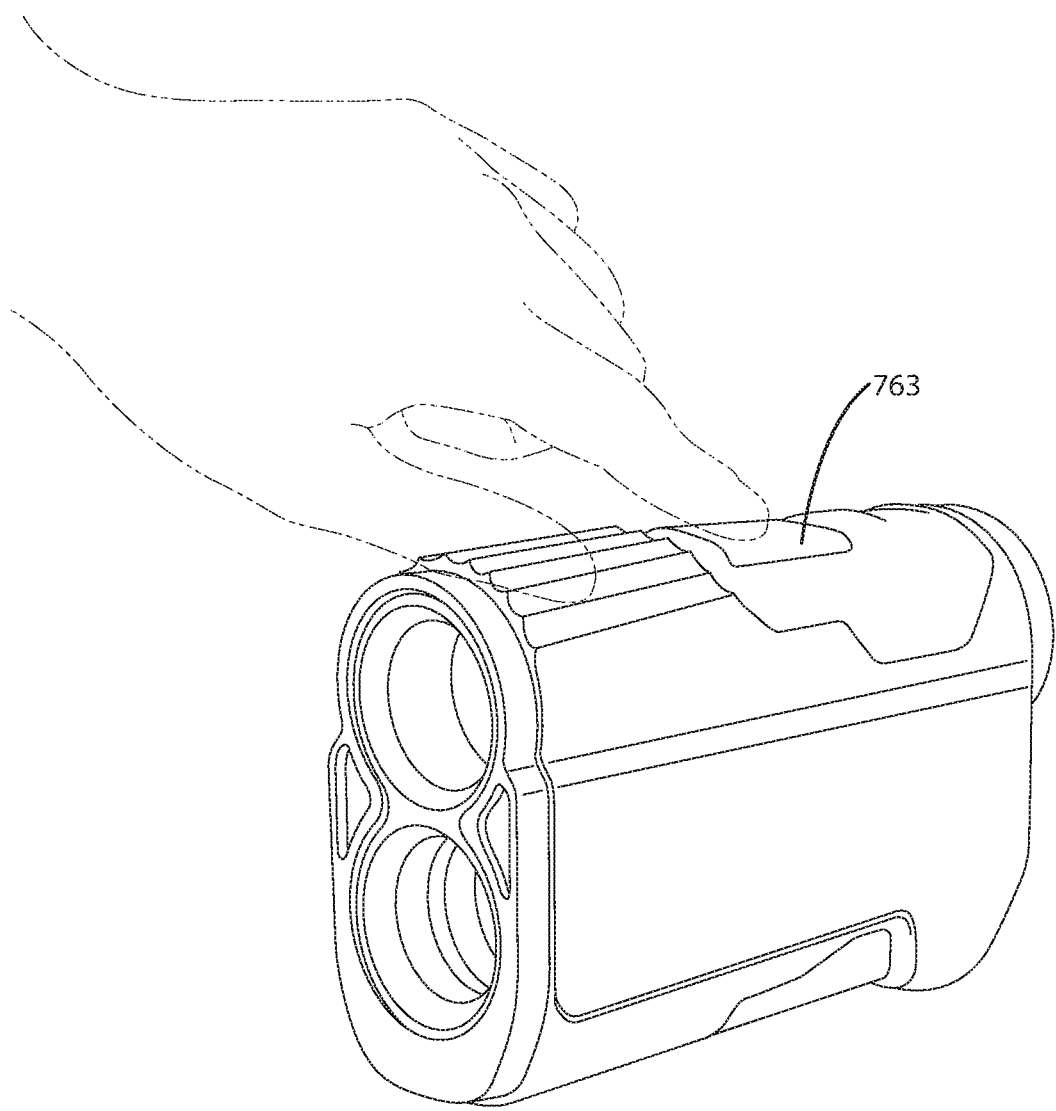
FIG. 24 is a perspective view of an alternative range finder having a thermoelectric module incorporated therein according to an eighth embodiment.
Figure 25:
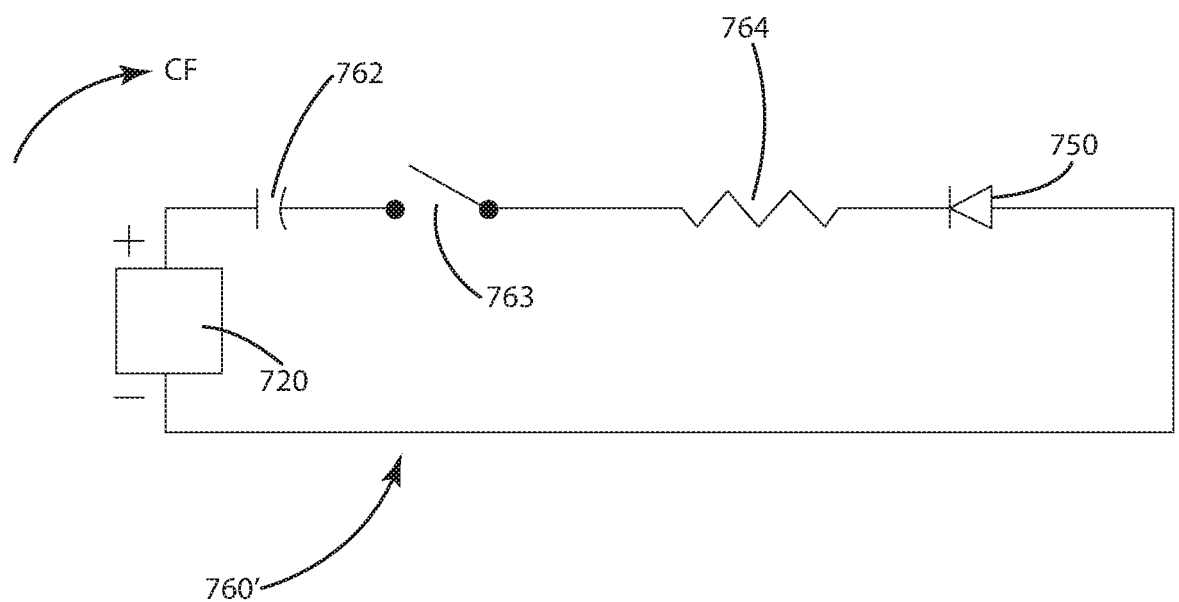
FIG. 25 is a diagram of a circuit for use with the range finder of FIG. 24 having a thermoelectric module incorporated therein.

Referring now to FIGS. 24 and 25, a range finder 710' similar to the range finder 710 is illustrated except for the inclusion of an on/off switch 763. The switch 763 can be incorporated into circuit 760' in a manner similar to that described above for the circuit 60 of FIGS. 8 and 8A. The switch 763 can be in the form of various switches, for example, toggle switches, push button switches, pressure switches, touch actuated switches, and the like. The switch 763 can be in the form of a touch actuated switch that is actuated by a user contacting an exterior surface of the switch 763. The circuit 760' can be electrically connected with the circuit 760 of FIG. 21 to selectively provide power to the components of the range finder 710', as described below.

With reference to FIG. 25, actuating the switch 763 closes and/or opens the switch 763 within the circuit 760'. This type of on/off switch 763 can be utilized in conjunction with capacitors and/or a battery. Voltage and/or electricity generated by the thermoelectric module 720 can be stored in the capacitor 762 or a battery. The user can effectively "charge" the capacitor while waiting for a target. For example, while sitting on a stand, a hunter can grasp the range finder 710', transferring the hunter's thermal energy to the thermoelectric module 720, which is then stored in the capacitor 762. When game or a target comes within the field of view of the hunter at a later time, the electricity stored in the capacitor and/or battery can be utilized by switching the switch 763 to the "on" position, such as by touching the touch actuated switch 763, as shown in FIG. 24. This in turn supplies power to the components of the range finder 710' electrically connected with the circuit 760', such as the light source 750, light receiving unit 760RU, distance calculation unit 760CU, and display unit 760DU to calculate and display the distance to the target object (FIG. 21). Optionally, an additional switching circuit that can stop the flow of electricity or voltage through the circuit thereby turning the components 750, 760RU, 760CU, and 760DU off until needed, can be provided if the capacitor 762 cannot store sufficient power.

An eighth alternative embodiment including a grasping element 870 for association with a projectile shooting device 801 is illustrated in FIGS. 26-32. This embodiment is similar in structure, function and operation to the other embodiments described herein with a few exceptions. For example, this construction can include a device 810, which can be any aiming device and/or a range finder described herein, such as the aiming devices 10, 110, 210, 310, 410, 510, 610 and/or rangefinder 710 of the embodiments above. Alternatively, the device 810 can be in the form of a flashlight, a laser, or any other type of device that consumes electricity and/or uses electricity to power a function of that device.

The grasping element 870 and device 810 can be mounted to a projectile shooting device 801, which can be any of the projectile shooting devices described in other embodiments herein, for example a firearm or rifle, which is shown as an M4 weapon system. Although shown in conjunction with a projectile shooting device, the grasping element and other devices of this embodiment can be joined with other types of items benefiting from a grasping element, such as a spotting scope, a camera, a rangefinder or similar items powered in part or whole by electricity.

Figure 33:
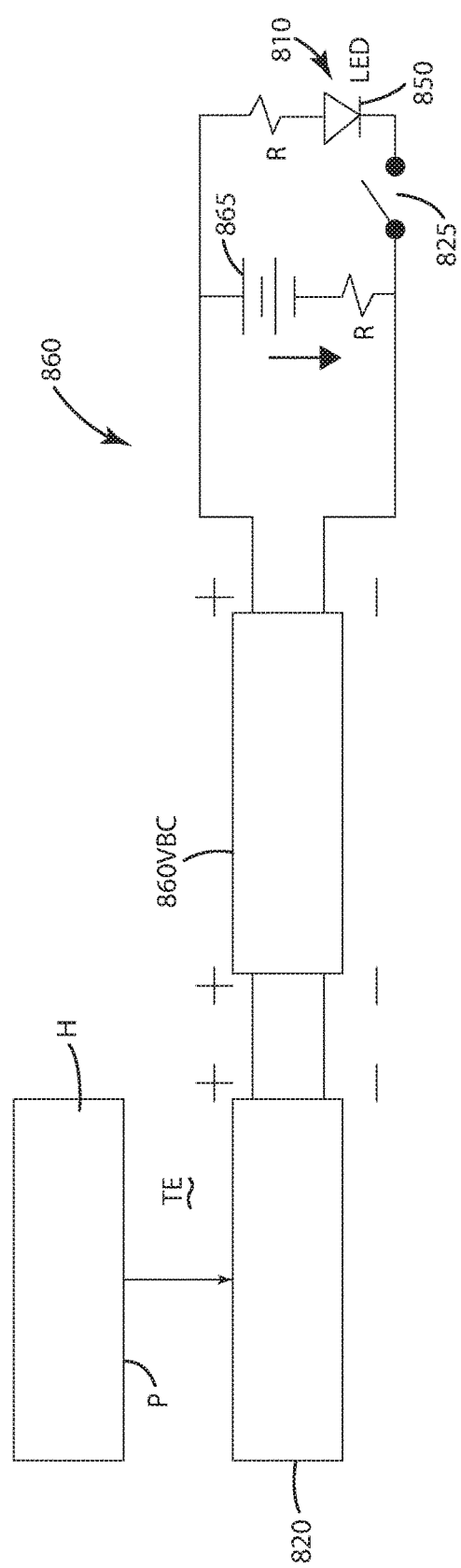
FIG. 33 is a circuit diagram with the manual actuator in an off mode and thermal energy being used to charge a power source, with an associated device being off.
Figure 34:
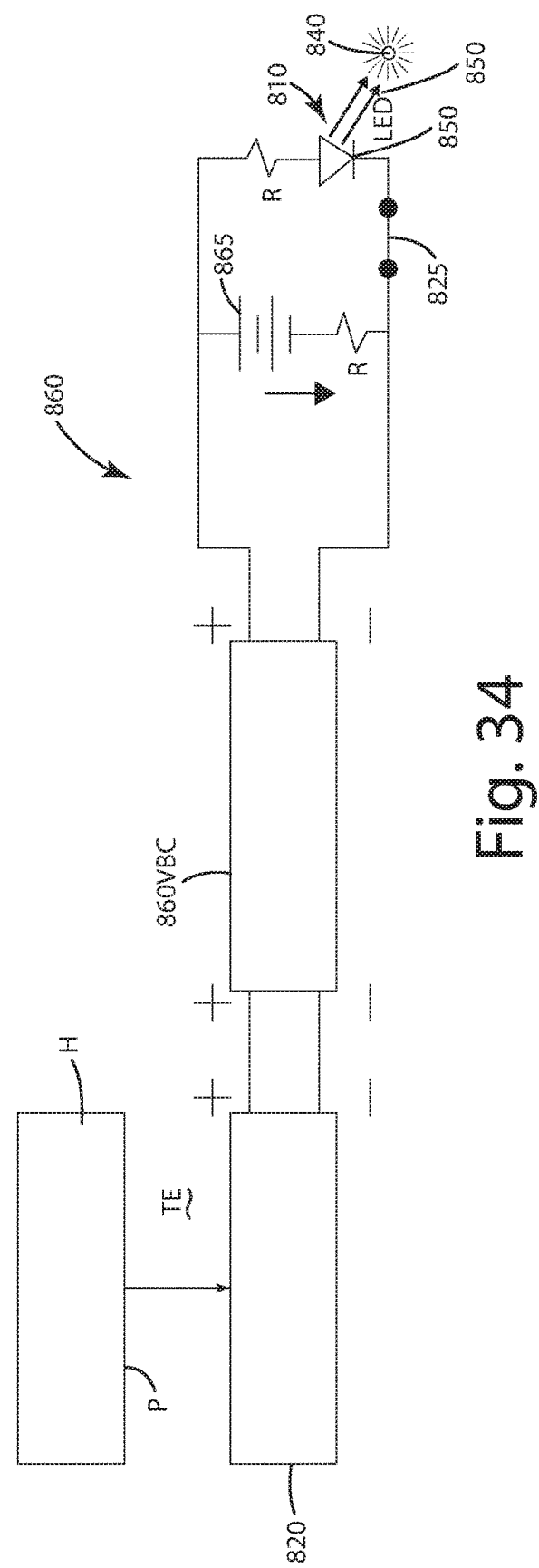

As illustrated, the device 810 can be in the form of an aiming device, such as a red dot scope. The device 810 can be mounted to the projectile shooting device 801 in any manner. In this construction, the device can include a light source 850 which can be associated with a circuit 860, as shown in FIGS. 33-34. This circuit 860 can be in electrical communication with a thermoelectric module 820 associated with the grasping element 870. The circuit 860, the thermoelectric module 820 and other components as described in further detail below can be associated with and/or disposed in the grasping element 870.

The grasping element 870 can be distal from the device 810, which is generally considered remote from the grasping element. For example the grasping element 870 can be optionally at least ½ inch, further optionally at least 1 inch, even further optionally at least 2 inches away from the device 810 when these components are mounted on an item, such as the projectile shooting device 801.

As described in further detail below, the thermoelectric module 820 can be in electrical communication with light source 850, when one is included in the device 810, via an electrical connector element 822 like those described in the other embodiments herein. As illustrated, that electrical connector device 822 can be in the form of a wire or power cable that extends from the device 810 to the grasping element 870. The power cable 822 can be plugged into an aiming device power receptacle 811 associated with the device 810. The other end of the power cable 822 can be plugged into a corresponding power receptacle 871, which can be defined at least partially within the grasping element 870 and optionally a rear grip 871 thereof. While shown as a DC cable and associated plugs, other types of electrical connector devices can be used, depending on the application. Further, electrical connector devices can be routed differently than as shown, depending on the item to which the grasping element and device are attached. In some cases, a physical connector device can be substituted with a Wi-Fi, Bluetooth or other wireless or power inductive component to transfer generated electricity from components in the grasping element 870 to the device 810.

Turning now to the grasping element 870 and its features, reference is made to FIGS. 26 and 30-34. The grasping element 870 can be in the form of a hand grip, such as a pistol grip for a firearm like that shown in FIG. 26. In other embodiments, shown for example in FIGS. 1-25, the grasping element can be in the form of a stock, a handle, a fore end and/or a hand guard configured to be joined with or otherwise form a portion of a projectile shooting device or other item with which the grasping element is used. The grasping element 870 can be contoured and configured to contact the user's hand and/or digits and thereby receive thermal energy from the user's body and/or other appendages during use. This thermal energy can be used to generate electricity with the thermoelectric module 820, which subsequently can be used to charge/recharge a power source 865 and/or directly or indirectly power the device 810.

Figure 29:
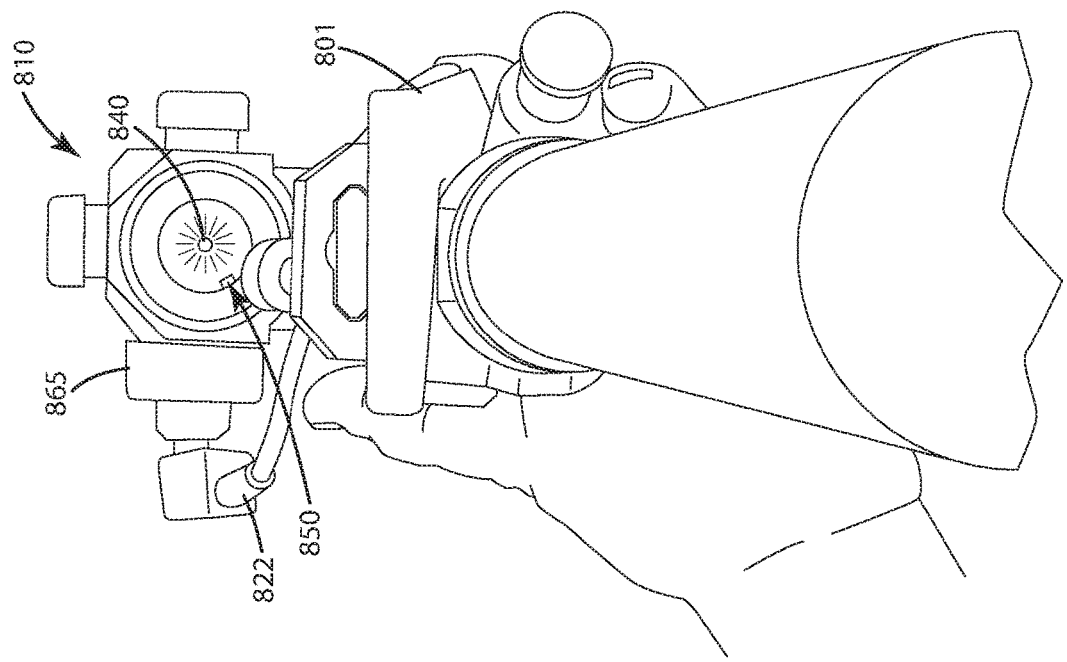
FIG. 29 is a rear perspective view of an aiming device associated with the grasping element and the thermoelectric module, with the manual actuator in an on mode, and a sight element visible in the device.
Figure 28:
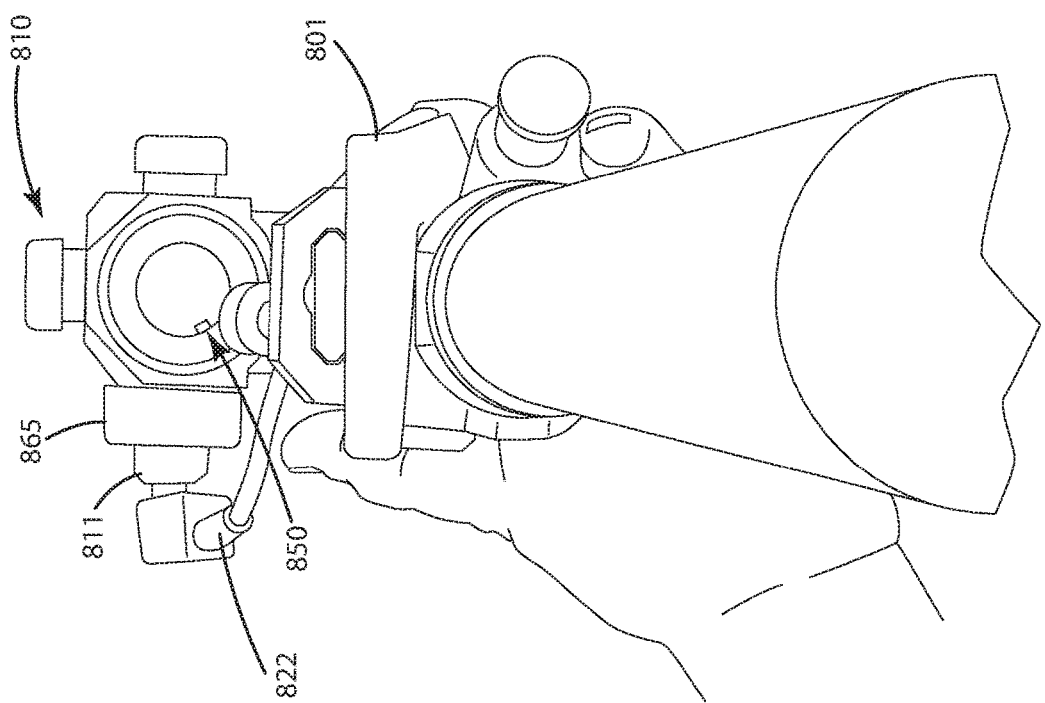
FIG. 28 is a rear perspective view of an aiming device associated with the grasping element and the thermoelectric module, with the manual actuator in an off mode.

The power source 865 can be a capacitor, a battery (chargeable and/or rechargeable), of the type described herein. The power source 865 can be disposed in a circuit 860 as shown in FIGS. 33 and 34. In some cases the power source 865 can be mounted in or on the grasping element. In other cases, the power source 865 can be mounted physically on the device 810, for example, as shown in FIGS. 28 and 29, where the power source 865 can optionally be a rechargeable battery mounted in a portion of the device 810.

Figure 32:
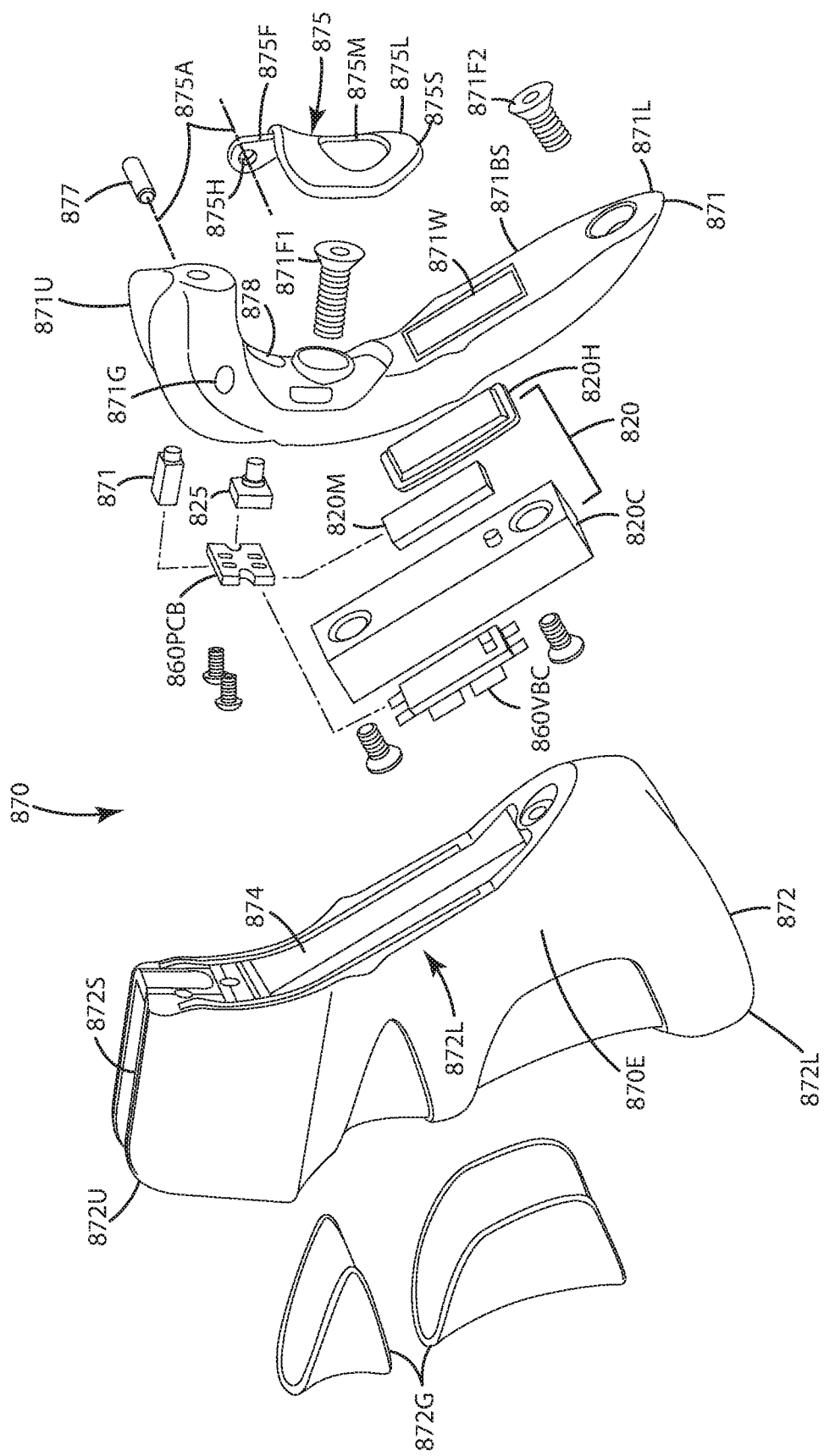
FIG. 32 is an exploded view of the grasping element.

The grasping element 870 as shown in FIG. 32 can include a front grip 872 and a rear grip 871. Collectively, the front grip and rear grip can form what is referred to as a hand grip. In other cases, the hand grip might not be divided into front and rear grips. Rather it can be a single integral component depending on the application.

The front grip 872 can define a slot 872S generally in the upper portion 872U of the front grip 872. The slot can be distal from the lower portion 872L of the front grip.

Figure 31:
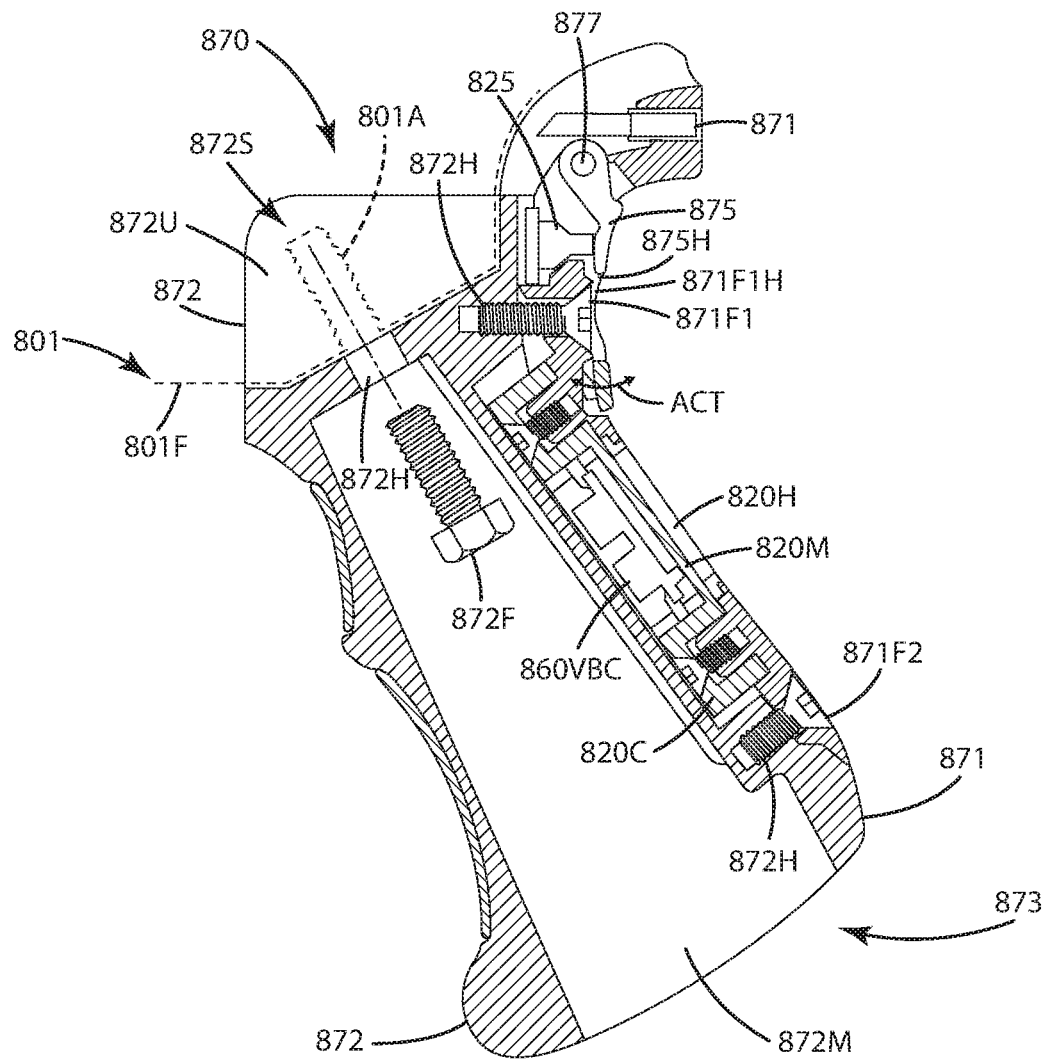
FIG. 31 is a section view of the grasping element taken along line 31-31 of FIG. 30.

The slot can be configured to receive a portion of the projectile shooting device 801, for example a pistol attachment flange 801F (shown in broken lines in FIG. 31). This flange can define and aperture 801 in which a fastener 872F can be advanced to secure the front grip 872, and thus the entire grasping element 870, to the projectile shooting device 801. The front grip can define a corresponding hole 872H through which the faster 872F fits to be able to be threaded into the aperture 801A of the flange 801F. Of course, the hand grip and/or grasping element 870 can be constructed to include other types of attachment mechanisms for joining the same with another item, such as the projectile shooting device 801. The precise type of mechanism and structure can be dictated by the device to which that grip is attached.

Optionally, the front grip 872 can include grip inserts 872G which optionally can be constructed from a different material than the remainder of the front grip 872. As an example, the front grip 872 can be constructed from a more rigid polymer or plastic material. The grips 872G can be constructed from an elastomeric, viscoelastic or other more tactile material, such as rubber, silicone and the like. These grips can fit within respective recesses defined by the front grip 872.

As mentioned above, the front grip 872 can be joined with a rear grip 871. Collectively or individually, these grips can be referred to as a housing 873. Again, these grips can be integrally formed with one another to form a unitary housing, or they can be separately constructed to form a multi-piece housing assembled from different components. The housing and the respective grips can be contoured so that the housing is configured to be manually grasped by a user. This can be accomplished by constructing the grasping element 870 so that its contours generally mimic that of the users hand or other appendage.

As shown, the rear grip 871 can be removably joined with the front grip 872. This can be accomplished via fasteners 871F1 and 872F2, which can be threaded into corresponding apertures 872H defined by the front grip 872. Of course, the holes and fasteners can be reversed according to the respective components. In other embodiments, the rear grip 871 can be fastened secured to the front grip 872 via other mechanisms, for example, pins, resilient tabs, snap lock features, adhesives, welds, and the like. In some cases it is suitable to ensure that the rear grip 871 is removable without extra effort from the front grip 872 so that service can be performed on the components associated with either.

The housing 873 can generally include an exterior surface 870E configured to engage a user's appendage, such as a user's hand 47. The housing 873 also can define an interior compartment 874. This interior compartment 874 can be cooperatively defined by a portion of the front grip 872 and a portion of the rear grip 871. This interior compartment 874 can extend along a spine 872L of the rear grip 871 along or adjacent a portion of the back strap 871BS of the rear grip 871. The interior compartment 874 can be sized to accommodate several other components as well. For example, the compartment 874 can be sized to receive the thermoelectric module 820 and its optional components, such as the module unit 820M, the hotplate 820H, and the cold sink 820C, as well as the voltage boost circuit 860VBC, the printed circuit board 860PCB, and the switch 825, which optionally can be in the form of a tactile switch, or some other type of switch as described in the embodiments herein. The interior compartment 874 can house the foregoing components and/or other components, optionally in a compartment separate from a front compartment 872M defined by the front grip 872. This interior compartment 874 can be closed off by joining the rear grip 871 with the front grip 872 as shown.

As mentioned above, and with reference to FIGS. 30-32, the rear grip 871 can be configured to be joined with the front grip 872 via fasteners 871F and 871F2. The rear grip 871 can comprise several components. For example, it can include a back strap 871BS. This back strap can be a portion of the housing, rear grip and grasping element in general that is configured to engage substantially a palm PM of a user's hand H. The back strap 871BS can define a window 871W through which a portion of the thermoelectric module 820 protrudes. For example the hotplate 820H can protrude at least partially through the window 871W and form a portion of the exterior surface of the housing, more generally a portion of the surface of the back strap 871BS. The hotplate 820H outer surface can be flush with the surface of the back strap 871BS. With the hotplate 820H of the thermoelectric module 820 so placed, that module can readily receive thermal energy TE from the users hand H and in particular the users palm P. This is illustrated schematically in FIGS. 33 and 34. Via the cooperation of the cold sink 820C of the thermoelectric module 820, and its placement within the interior compartment, distal from the hotplate 820H, a thermal gradient is produced relative to the thermoelectric module as described in connection with the embodiments above. The cold sink 820C of the thermoelectric module 820, which can be a large piece of metal, is distal from the exterior surface 870E of the grasping element 870, and engaged by the user's hand H. This can facilitate the transfer of thermal energy rapidly through the module 820M of the thermoelectric module 820. In turn, this can increase the generation of electricity by the thermoelectric module 820. Optionally, the thermoelectric module 820 can be placed in a location on the grasping element 870 sufficient to absorb thermal energy TE from a user's body when the projectile shooting device is brought to a shooting position or into a field of view of the user.

Figure 26:
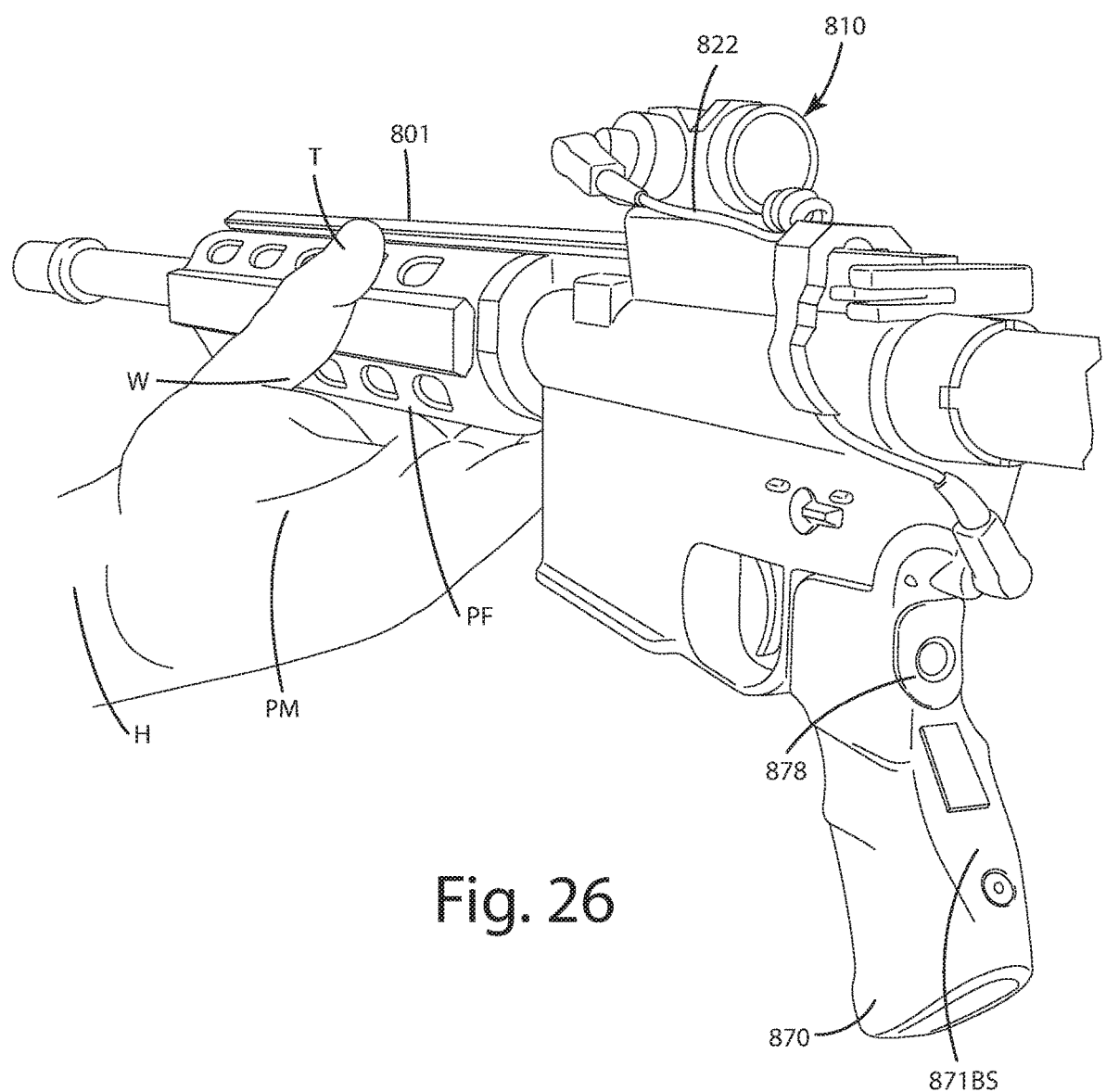
FIG. 26 is a perspective view of a grasping element including a manual actuator associated with a thermoelectric module, installed on a projectile shooting device, according to an eighth alternative embodiment.
Figure 27:
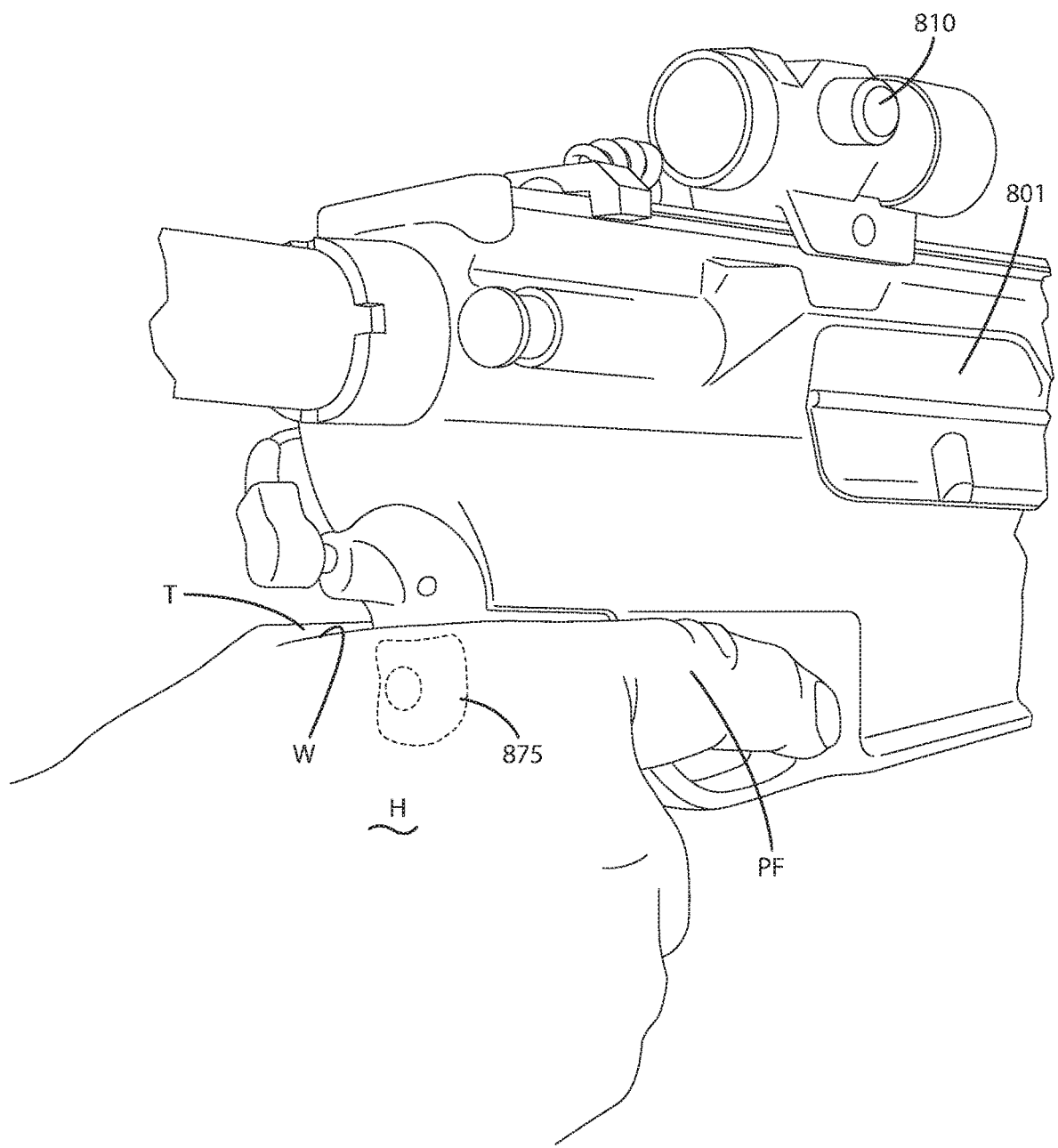
FIG. 27 is a perspective view of the grasping element being engaged by an appendage of a user to actuate the manual actuator.
Figure 30:
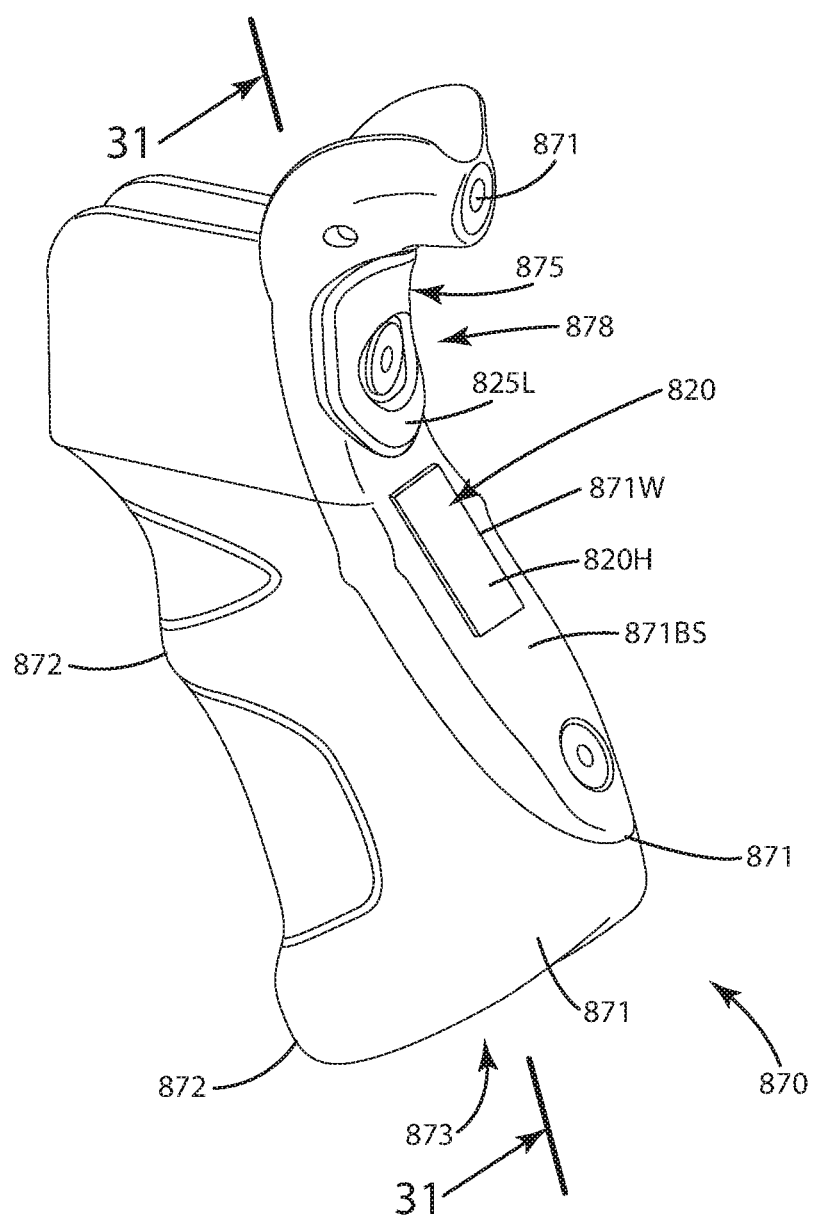
FIG. 30 is a rear perspective view of the grasping element removed from a projectile shooting device.

The thermoelectric module 820 can be exposed through the back strap 871BS through a window 871W. The back strap 871BS can be placed at a location closer to the lower end 871L of the rear grip 871. Likewise, the thermoelectric module 820 can be disposed closer to the lower end 871L than the upper end 871U of the rear grip 871. As shown in FIGS. 30 and 32, the rear grip 871 can include a recessed portion 878 above the back strap 871BS, located on the rearward portion of the grasping element 870. This recess portion is disposed below the upper portion 871U of the grasping element 870. This recessed portion 878 can be U- or V-shaped so that a portion of the web W of a user's hand H (the web being generally between the thumb and the pointer finger PF as shown in FIG. 26) can seat and nest within that recessed portion 878. This in turn can provide a positive indexing location for the hand relative to the grasping element 870. Of course, in other types of grips, this recessed portion can be minimized or in some cases eliminated or replaced with some other type of indexing feature.

Within the recessed portion 878, a manual actuator 875 can be disposed. This manual actuator 875 can include an actuator lever 875L which bends, hinges, pivots, rotates and/or otherwise moves relative to the rear grip and the housing in general. Movement can be dynamic, such as when the lever bends dynamically along a region, or truly rotational, such as when the lever pivots about a fixed pivot axis. Optionally, for the latter, the lever 875L includes a pivot axis 875A about which the lever 875L rotates. The actuator lever 875L can include a first end 875F defining a hole 875H through which pivot pin 877 is placed. Pivot pin 877 also can extend through a rear grip hole 871G. The pin 877 can be staked, screwed and or friction fit through the hole 871G so that the pin and actuator lever 875L are securely mounted to the housing, grasping element and more particularly the rear grip 871.

The first end 875F of the actuator lever 875L can be pivotally joined with a housing and rear grip of the manual actuator 875. The second and 875S of the actuator lever 875L, which is distal from the first end, can be generally free and can move toward and away from the housing when the actuator lever 875L moves in direction ACT as shown in FIG. 31. This movement of the actuator lever 875L and generally the manual actuator, relative to the hand grip can be affected by movement of the user's hand H relative to the hand grip 870. For example, when a user presses the web W of their hand H against the manual actuator 875, it moves the actuator about the axis. Of course, where dynamic movement such as bending is suitable, the lever first end can be fixed to a base and generally cantilevered to form a cantilever, but bendable or flexible so the free second end can move.

Optionally, the manual actuator 875 can define a hole 875M through which the fastener 871F1 can extend to secure the rear grip 871 to the front grip 872, yet still enable the manual actuator 875 to be moved relative to the housing. Further optionally, the manual actuator can be distal from the thermoelectric module 820. For example, the thermoelectric module 820 can be disposed below the manual actuator 875 a preselected distance. This can enable a user to engage the thermoelectric module 822 to transfer thermoelectric energy TE from the palm P to the thermoelectric module. The user also can selectively but separately move their hand H so that the web W of their hand H engages or does not engage the manual actuator 875. In this manner, a user can grasp their hand around the grasping element 870 to hold the weapon, use their palm P to transfer thermoelectric energy TE to the thermoelectric module 820 and generate electricity be of the same, yet keep another portion of their hand, that is the web W, from moving or otherwise engaging the manual actuator 875. Thus, the user U can generate electricity, optionally charging or recharging the power source 865, but not transferring the generated electricity to the device 810 to actuate the device or otherwise power a component, light source or other feature of the device. With a slight movement of hand, the user can grasp the hand grip 870 in which case the web W pushes against the actuator 875 to cause transmission or transfer of the generated electricity from the thermoelectric module to the device 810 to power the device or a component thereof so that a user can utilize the associated feature.

The manual actuator 875 as mentioned above includes can include actuator lever 875L and a switch 825. The switch 825 can be the tactile button switch. The actuator lever 875L can be configured so that when it moves inward, generally toward the front grip 872, the interior surface of the actuator lever 875L engages the tactile button switch 825. This tactile button switch can be in electrical communication with a printed circuit board 860PCB. Activation or deactivation of the button switch, as described below, can operate the device and/or provide charging or discharging of the power source, or otherwise cause generated electricity from the thermoelectric module to be directly or indirectly transferred to the device 820 as described in further detail below. Optionally, the tactile button switch can be mounted under the actuator lever, generally between the first and second ends of the actuator lever.

The switch 825 is in electrical communication with a circuit 860, as illustrated in FIGS. 33 and 34. The switch 825 is operable in an open mode relative to the circuit as shown in FIG. 33. The switch achieves this open mode when the manual actuator 875 is in an off mode, generally undepressed or unengaged by the user. While the hand H or palm P is on the grip 870, thermal energy creates a thermal gradient across the thermoelectric module 820 causing the module to generate electricity. In this open mode of the switch, the generated electricity from the thermoelectric module can optionally be transferred to the power source 865 in the circuit to charge and/or recharge that power source.

In some embodiments, the generated electricity from the thermoelectric module 820 passes to the voltage boost circuit 860VBC, otherwise referred to as the voltage booster herein, to boost the voltage from the thermoelectric module 820 optionally above 1 V, further optionally above 2 V, even further optionally above 4 volts, yet further optionally to a voltage range of about 2 V to about 12 V. Where the circuit 860 is in communication with a power source 865 that is rechargeable, that generated electricity from the thermoelectric module, optionally boosted above the voltage levels noted above, can recharge the power source 865. The power source subsequently can store a portion or all of that generated electricity until the generated electricity is later discharged or otherwise electrically communicated to the device 810 when the switch is in the closed mode and the manual actuator is in the on mode.

As mentioned above, the switch 825 can be operable in a closed mode when the manual actuator is in an on mode, for example as shown in FIG. 34. This on mode for the manual actuator can be achieved when the manual actuator 875 is engaged in optionally depressed by the user's appendage, for example the web W, inward relative to the rear grip 871 and the hand grip 870. Thermal energy from the hand H and palm P is being conducted into the thermoelectric module 820 causing the module to produce power which in turn is being boosted by to usable voltage levels by the voltage boost circuit 860VBC. The boosted power being produced by the voltage boost circuit is used to recharge the power source 865 and any excess power rejected by the power source (which again can be any energy storage device) can be redirected to provide power to the device.

More particularly, in the closed mode shown in the circuit 860 of FIG. 34, the switch 825 facilitates electrical communication between the power source 865 and the device 810 whereby the power source powers the device and its components. Where the device optionally includes a light source 850, that light source 850 can be illuminated via the generated electricity from the thermoelectric module 820 (although that generated electricity optionally may have been boosted by the voltage booster and/or previously stored for a time in the power source). The light source 850 can be configured to illuminate a sighting element 840 associated with the device, in any of the manners described in the other embodiments herein. Optionally, where the device is in the form of a rangefinder or other device, that device can be powered by the generated electricity to enable the device to function in any of the manners described in other embodiments herein.

Where a power source 865 is provided in the circuit 860 to provide electricity or voltage to the device 810, the thermoelectric module 820 can be considered to indirectly power the device because, technically, the generated electricity is flowing from the power source. Where no power source is included in the circuit, the thermoelectric module can be considered to directly power the device, with the generated electricity flowing from that thermoelectric module to the device requiring electricity to power some feature or function. In either case, the generated electricity that came directly or indirectly from the thermoelectric module can be eventually transferred to the device. It is also to be noted that generated electricity produced by the thermoelectric module is still considered generated electricity herein, whether or not that generated electricity has been boosted by voltage booster circuit, and whether or not that generated electricity has been stored in and/or discharged from a power source.

Operation of the grasping element and device of the current embodiments will now be described. The grasping element 870, such as a hand grip, is mountable to an item, such as a projectile shooting device 801. The grasping element 870 can be utilized to power and/or control a device 810, such as a sighting element, rangefinder, light or other electric device. The grasping element 870 can include a thermoelectric module 820 positioned to experience or undergo a thermal gradient as a result of the transfer of thermal energy TE from an appendage of a user placed in proximity to the grasping element 870. As shown herein, that appendage can be a hand H, and in particular a palm P (FIG. 27) that can engage the thermoelectric module 820. The thermoelectric module 820 can generate electricity due to the thermal gradient produced across it. That generated electricity can be conveyed in a circuit 860 within which the thermoelectric module 820 is disposed. Optionally the generated electricity can be boosted to the levels noted above by voltage boost circuit 860VBC. The generated electricity also can be stored in a power source 865, and/or used to recharge the power source, depending on the application and whether or not that power source is incorporated into the circuit and/or device 810.

The circuit 860 can be controlled via the manual actuator 875. When this manual actuator is not engaged by the user, the manual actuator can be an off mode. In this off mode, the manual actuator 875 does not adequately engage the pressure button switch 825, and thus the switch remains in an open mode as shown in FIG. 33. In this manner, the thermoelectric module 820, optionally boosted by the voltage booster 860VBC charges and/or recharges the power source 865. The device 810, however, remains unpowered. Thus, as shown in FIG. 28, the device 810 may not have an illuminated sighting element within it. However, when the user depresses the manual actuator 875 with the web of their hand H and the actuator moves relative to the grip, the tactile button switch 825 is depressed which in turn closes that switch 825 as shown in FIG. 34 within the circuit 860. This enables electrical communication of the generated electricity originating from the thermoelectric module 820 to be conveyed to the device 810, optionally from the power source 865. This in turn illuminates the sighting element 840 as shown in FIG. 29 so that that sighting element is visible or illuminated within the field of view of a user aiming the projectile shooting device 801. When the manual actuator 875 is so engaged, it is considered to be in the on mode, which in turn translates the pressure button switch 825 to the closed mode. Of course, other setups for the circuit the respective switching actuators are contemplated herein.

It will be noted that the grasping element and associated manual actuator herein can be helpful. For example, the user can turn off the circuit to prevent complete discharge of the power source when the device 810 is not being used. When a user desires to utilize the device 810, the user can manually engage the manual actuator to turn it to the on mode, in which case the circuit is closed and the generated electricity can be utilized by the device. In this way, the available power that is stored in the power source can be preserved well.

It also will be noted that the position of the thermoelectric module and the manual actuator relative to the hand grip is particularly suitable for a variety of applications. For example, the manual actuator is located on the grip in the recessed portion, which again corresponds to the web between a user's thumb and pointer finger or forefinger. This portion of the user's hand corresponds to an area of the palm containing mostly skin and soft tissue. This location can be helpful because it provides a high level of comfort to the user, even when gripping a contoured or generally uneven surface, such as that of the hand grip. The actuator lever itself can be constructed with sufficient surface area such that the soft tissue of the web is capable of acting against that surface area to actuate a variety of force switches, which can be actuated under a range of different forces. Conversely, since the underlying tissue in the web W is soft, it can be incapable of directly actuating very low force switches when the surface area of those switches are small, for example the actuation stems of tactile button switches. In addition, the manual actuator is well suited for universal, ambidextrous use because it is on a portion of the grip that a hand, whether left or right, typically will engage as a user handles the grasping element on the device.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. Any reference to claim elements as "at least one of X, Y and Z" is meant to include any one of X, Y or Z individually, and any combination of X, Y and Z, for example, X, Y, Z; X, Y; X, Z; and Y, Z.

The embodiments of the invention in which an exclusive property or privilege is claimed are defined as follows:

1. A manual grasping element comprising:
   a housing contoured so that the housing is configured to be manually grasped by a user, the housing including an exterior surface and defining an interior compartment;
   a manual actuator moveably joined with the housing adjacent the exterior surface;
   a thermoelectric module disposed adjacent the exterior surface so that thermal energy from a user's body is transferred to the thermoelectric module when the housing is grasped by a user,
   wherein the thermoelectric module is configured to generate electricity sufficient to power a device remote from the housing as a result of thermal energy transferred from the user's body,
   wherein the manual actuator is operable in an on mode, in which the manual actuator enables transfer of the generated electricity to the device, and an off mode, in which the manual actuator does not enable transfer of the generated electricity to the device,
   wherein the manual actuator is convertible from the off mode to the on mode while the thermal energy is transferred from the user's body to the thermoelectric module, and while the housing is grasped by the user so that the device actuates via the generated electricity while the housing is grasped by the user.

2. A manual grasping element comprising:
   a housing contoured so that the housing is configured to be manually grasped by a user, the housing including an exterior surface and defining an interior compartment;
   a manual actuator moveably joined with the housing adjacent the exterior surface;
   a thermoelectric module disposed adjacent the exterior surface so that thermal energy from a user's body is transferred to the thermoelectric module when the housing is grasped by a user,
   wherein the thermoelectric module is configured to generate electricity sufficient to power a device remote from the housing as a result of thermal energy transferred from the user's body,
   wherein the manual actuator is operable in an on mode, in which the manual actuator enables transfer of the generated electricity to the device, and an off mode, in which the manual actuator does not enable transfer of the generated electricity to the device,
   wherein the manual actuator includes an actuator lever that is movably joined with the housing at a first end of the manual actuator,
   wherein the manual actuator includes a second end distal from the first end that is free and can move toward and away from the housing.

3. The manual grasping element of claim 2,
   wherein the manual actuator is distal from the thermoelectric module,
   wherein the manual actuator includes a tactile button switch mounted under the actuator lever between the first and second ends, the tactile button switch being in electrical communication with the thermoelectric module.

4. The manual grasping element of claim 3,
   wherein the housing is a hand grip including a front grip and a rear grip,
   wherein the front grip and rear grip cooperatively define the interior compartment,
   wherein the rear grip is removably joined with the front grip,
   wherein the rear grip includes a pivot pin that is joined with the manual actuator so that the manual actuator is pivotally joined with the housing.

5. The manual grasping element of claim 4,
   wherein the thermoelectric module is in electrical communication with a circuit comprising a voltage booster,
   wherein the voltage booster is configured to provide a voltage output in the range of about 2 to 12 Volts.

6. A manual grasping element comprising:
   a housing contoured so that the housing is configured to be manually grasped by a user, the housing including an exterior surface and defining an interior compartment;
   a manual actuator moveably joined with the housing adjacent the exterior surface;
   a thermoelectric module disposed adjacent the exterior surface so that thermal energy from a user's body is transferred to the thermoelectric module when the housing is grasped by a user, wherein the thermoelectric module is configured to generate electricity sufficient to power a device remote from the housing as a result of thermal energy transferred from the user's body, wherein the manual actuator is operable in an on mode, in which the manual actuator enables transfer of the generated electricity to the device, and an off mode, in which the manual actuator does not enable transfer of the generated electricity to the device, wherein the thermoelectric module is in electrical communication with a circuit comprising a voltage booster, wherein the circuit and voltage booster are disposed in the interior compartment of the housing, wherein the housing includes a rear grip and a front grip, wherein the front grip defines a slot configured to receive a portion of a projectile shooting device, wherein the rear grip includes a back strap adjacent which the thermoelectric module is disposed so that the thermoelectric module is configured to receive thermal energy from a portion of a palm of a user, wherein the rear grip includes a recessed portion above the back strap in which the manual actuator is disposed so that the manual actuator is configured to engage a web of a user's hand between a pointer finger and a thumb of the user.

7. The manual grasping element of claim 6 comprising:
wherein the thermoelectric module includes a hot plate and a cold sink in the interior compartment,
wherein the hot plate is adjacent the exterior surface of the housing, the hot plate configured to engage a palm of a user; and
wherein the cold sink is disposed in the interior compartment, distal from the hot plate.

8. The manual grasping element of claim 1 wherein the exterior surface defines a slot distal from the manual actuator, the slot configured to receive a portion of a projectile shooting device within the slot.

9. A manual grasping element comprising:
a housing contoured to form a hand grip for a projectile shooting device, the hand grip including a rear grip;
a manual actuator movably joined with the rear grip on a rearward, hand facing region of the rear grip;
a thermoelectric module disposed in the rear grip, in the hand facing region of the rear grip so that thermal energy from a user's hand is transferred to the thermoelectric module to generate electricity when the housing is grasped in the user's hand,
wherein the manual actuator is operable in an on mode attained when the hand grip is grasped by the user's hand, in which the manual actuator enables transfer of the generated electricity to a remote device, and an off mode attained a period after the hand grip is released from the user's hand, in which the manual actuator does not enable transfer of the generated electricity to the remote device so that the generated electricity does not inadvertently drain.

10. The manual grasping element of claim 9,
wherein the manual actuator includes a switch in electrical communication with the circuit,
wherein the switch is operable in an open mode while the manual actuator is in the off mode, so that the generated electricity from the thermoelectric module can be boosted above 2 volts,
wherein the switch is operable in a closed mode while the manual actuator is in the on mode.

11. The manual grasping element of claim 10, comprising:
a power source that is rechargeable and in electrical communication with the circuit and the remote device,
wherein the generated electricity from the thermoelectric module boosted above 2 volts recharges the power source while the switch is in the open mode, the power source subsequently storing the generated electricity.

12. The manual grasping element of claim 9,
wherein the generated electricity produces a dot sight element that is projected on a lens so a user can align the dot sight element with a target.

13. The manual grasping element of claim 9,
wherein the housing defines a slot within which a portion of a projectile shooting device extends.

14. A manual grasping element comprising:
a housing contoured to form a hand grip for a projectile shooting device, the hand grip including a rear grip;
a manual actuator movably joined with the rear grip on a rearward, hand facing region of the rear grip;
a thermoelectric module disposed in the hand grip so that thermal energy from a user's hand is transferred to the thermoelectric module to generate electricity when the housing is grasped in the user's hand,
a voltage booster disposed in the hand grip,
a circuit disposed in the hand grip and in electrical communication with the thermoelectric module and the voltage booster,
wherein the manual actuator is operable in an on mode, in which the manual actuator enables transfer of the generated electricity to a remote device, and an off mode, in which the manual actuator does not enable transfer of the generated electricity to the remote device,
a power cable in electrical communication with the circuit, the power cable extending to a location distal from the hand grip to the remote device, which is mounted on the projectile shooting device.

15. A manual grasping element comprising:
a housing contoured to form a hand grip for a projectile shooting device, the hand grip including a rear grip;
a manual actuator movably joined with the rear grip on a rearward, hand facing region of the rear grip;
a thermoelectric module disposed in the hand grip so that thermal energy from a user's hand is transferred to the thermoelectric module to generate electricity when the housing is grasped in the user's hand,
a voltage booster disposed in the hand grip,
a circuit disposed in the hand grip and in electrical communication with the thermoelectric module and the voltage booster,
wherein the manual actuator is operable in an on mode, in which the manual actuator enables transfer of the generated electricity to a remote device, and an off mode, in which the manual actuator does not enable transfer of the generated electricity to the remote device,
wherein the hand grip includes a back strap, adjacent which the thermoelectric module is disposed, so that the thermoelectric module can receive thermal energy from a palm of a user,
wherein the hand grip includes a recessed portion above the back strap in which the manual actuator is disposed so that the manual actuator is configured to engage a web of a user's hand between a pointer finger and a thumb of the user,
whereby the web can actuate the manual actuator to the on mode or the off mode.

16. A method of operating a grasping element, the method comprising:
- providing a grasping element in the form of a hand grip mountable to a projectile shooting device, the grasping element including therein a thermoelectric module positioned to experience a thermal gradient as a result of the transfer of thermal energy from an appendage of a user;
- generating electricity with the thermoelectric module due to the thermal gradient; and
- engaging a manual actuator with the appendage of the user to convert the manual actuator from an off mode, in which the manual actuator does not enable transfer of the generated electricity to a remote device, to an on mode, in which the manual actuator enables transfer of the generated electricity to the remote device to power the remote device,
- wherein the grip includes a protruding back strap below a recessed portion within which the manual actuator is located, the manual actuator being movable relative to the hand grip when engaged by the appendage.

17. A method of operating a grasping element, the method comprising:
- providing a grasping element in the form of a hand grip mountable to a projectile shooting device, the grasping element including therein a thermoelectric module positioned to experience a thermal gradient as a result of the transfer of thermal energy from an appendage of a user;
- generating electricity with the thermoelectric module due to the thermal gradient; and
- engaging a manual actuator with the appendage of the user to convert the manual actuator from an off mode, in which the manual actuator does not enable transfer of the generated electricity to a remote device, to an on mode, in which the manual actuator enables transfer of the generated electricity to the remote device to power the remote device,
- wherein the hand grip includes a back strap adjacent which the thermoelectric module is disposed so that the thermoelectric module can receive the thermal energy from the a palm of the appendage of the user,
- wherein the hand grip includes a recessed portion above the back strap in which the manual actuator is disposed,
- wherein during the engaging step, the manual actuator engages a web of the appendage of the user, the web being between a pointer finger and a thumb of the user, the manual actuator moving forwardly toward the hand grip during the engaging step.

18. The method of claim 16 comprising:
providing a rechargeable power source;
establishing electrical communication between the thermoelectric module and the rechargeable power source; and
charging the rechargeable power source with the electricity generated by the thermoelectric module while the manual actuator is in the off mode.

19. The method of claim 16 comprising:
providing a voltage booster in the hand grip;
establishing electrical communication between the thermoelectric module and the voltage booster; and
increasing a voltage of the electricity generated by the thermoelectric module and supplied to a rechargeable power source.

20. The method of claim 19 wherein the voltage booster is configured to provide a voltage output in the range of about 2 to 12 Volts.

* * * * *